US012662695B2

(12) United States Patent
Wei et al.

(10) Patent No.: US 12,662,695 B2
(45) Date of Patent: Jun. 23, 2026

(54) NON-INVASIVE GENE MUTATION DETECTION IN LUNG CANCER PATIENTS

(71) Applicant: THE REGENTS OF THE UNIVERSITY OF CALIFORNIA, Oakland, CA (US)

(72) Inventors: Fang Wei, North Hills, CA (US); David T.W. Wong, Beverly Hills, CA (US); Wu-Chou Su, Tainan (TW)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 224 days.

(21) Appl. No.: 17/931,205

(22) Filed: Sep. 12, 2022

(65) Prior Publication Data

US 2023/0127823 A1 Apr. 27, 2023

Related U.S. Application Data

(63) Continuation of application No. 15/313,301, filed as application No. PCT/US2015/034028 on Jun. 3, 2015, now abandoned.

(60) Provisional application No. 62/007,286, filed on Jun. 3, 2014.

(51) Int. Cl.

| | |
|---|---|
| *C12Q 1/68* | (2018.01) |
| *C12Q 1/6825* | (2018.01) |
| *C12Q 1/6886* | (2018.01) |
| *G01N 27/327* | (2006.01) |
| *G01N 33/543* | (2006.01) |
| *G01N 33/5752* | (2026.01) |

(52) U.S. Cl.
CPC ......... *C12Q 1/6825* (2013.01); *C12Q 1/6886* (2013.01); *G01N 27/3276* (2013.01); *G01N 33/5438* (2013.01); *G01N 33/5752* (2026.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2011/0027782 A1 | 2/2011 | Haake |
| 2011/0207622 A1 | 8/2011 | Wong |
| 2012/0077201 A1 | 3/2012 | Varmus |

FOREIGN PATENT DOCUMENTS

| | | |
|---|---|---|
| CN | 101400993 | 4/2009 |
| CN | 102906275 | 1/2013 |
| CN | 102959091 | 3/2013 |
| WO | 2007059167 | 5/2007 |
| WO | 2010151817 | 12/2010 |
| WO | 2011100483 | 8/2011 |
| WO | 2012002477 | 1/2012 |
| WO | 2012162563 | 11/2012 |
| WO | 2013055234 | 4/2013 |

OTHER PUBLICATIONS

Endo et al; Lung Cancer, vol. 50, pp. 375-384, 2005 (Year: 2005).*
Liao et al; Journal of Molecular Diagnostics, vol. 9, Apr. 2007, pp. 158-168 (Year: 2007).*
Wei et al; Clinical Cancer research, vol. 15, pp. 4446-4452; Jul. 2009 (Year: 2009).*
A. Jasmijn Hubers et al., "EGFR mutation analysis in sputum of lung cancer patients: A multitechnique study", Lung Cancer., NL, (Oct. 1, 2013), vol. 82, No. 1, doi:10.1016/j.lungcan.2013.07.011, ISSN 0169-5002, pp. 38-43, XP055431203.
Al-Nedawi et al., "Intercellular transfer of the oncogenic receptor EGFRvIII by microvesicles derived from tumour cells," May 2008, Nature Cell Biology, 10(5):619-644.
Bai et al., "Epidermal Growth Factor Receptor Mutations in Plasma DNA Samples Predict Tumor Response in Chinese Patients With Stages IIIB to IV Non-Small-Cell Lung Cancer," Jun. 2009, Journal of Clinical Oncology, 27(16):2653-2659.
Bidard et al., "Going with the Flow: From Circulating Tumor Cells to DNA," Oct. 2013, Science Translational Medicine, 5(207):1-7.
Chin et al. "Detection of Epidermal Growth Factor Receptor Variations by Partially Denaturing HPLC," 2007, Clinical Chemistry, 53(1):62-70.
Gerlinger et al., "Intratumor Heterogeneity and Branched Evolution Revealed by Multiregion Sequencing," Mar. 2012, N Engl J Med., 366(10): 883-892.
Guescini et al., "C2C12 myoblasts release micro-vesicles containing mtDNA and proteins involved in signal transduction," 2010, Experimental Cell Research, 316:1977-1984.
Janne et al., "ARapid and Sensitive EnzymaticMethod for Epidermal Growth Factor Receptor Mutation Screening," Feb. 2006, Clin Cancer Res, 12(3):751-758.
Kahlert et al., "Identification of Doublestranded Genomic DNA Spanning All Chromosomes with Mutated KRAS and 053 DNA in the Serum Exosomes of Patients with Pancreatic Cancer," Feb. 2014, 289(7):3869-3875.
Kimura et al., "Detection of Epidermal Growth Factor Receptor Mutations in Serum as a Predictor of the Response to Gefitinib in Patients with Non-Small-Cell Lung Cancer," Jul. 2006, Clin Cancer Res, 12(13):3915-3921.

(Continued)

*Primary Examiner* — Jehanne S Sitton

(74) *Attorney, Agent, or Firm* — Riverside Law LLP

(57) ABSTRACT

A system and method for the detection of saliva biomarkers in bodily fluids is described. In particular, the system is suitable for detecting biomarkers of lung cancer in a subject. The system includes an electrochemical sensor chip having at least one well, wherein the at least one well contains a working electrode coated with a conducting polymer functionalized with at least one capture probe, and at least one labeled detector probe. When the at least one labeled detector probe is mixed with a sample of the subject containing a biomarker of lung cancer and added to the at least one well, an electric current is applied to the sample, such that when at least some of the biomarker binds to the capture probe, a measurable change in electric current in the sample is created that is indicative of lung cancer.

3 Claims, 9 Drawing Sheets

Specification includes a Sequence Listing.

(56)                    References Cited

OTHER PUBLICATIONS

Kimura et al., "Evaluation of epidermal growth factor receptor mutation status in serum DNA as a predictor of response to Gefitinib (IRESSA)," 2007, British Journal of Cancer, 97:778-784.

Korri-Youssoufi et al., "Electrochemical biosensing of DNA hybridization by ferrocenyl groups functionalized polypyrrole", Analytica Chimica Acta, (20020000), vol. 469, pp. 85-92, XP002604413.

Lau et al., "Breast Cancer Exosome-like Microvesicles and Salivary Gland Cells Interplay Alters Salivary Glan Cell- Derived Exosome-like Microvesicles In Vitro," Mar. 2012, PLoS One, 7(3):e33037, pp. 1-9.

Lau et al., "Role of Pancreatic Cancer-derived Exosomes in Salivary Biomarker Development," Sep. 2013, The Journal of Biological Chemistry, 288(37):26888-26897.

Li et al., "Salivary Transcriptome Diagnostics for Oral Cancer Detection." Clinical Cancer Research. vol. 10, No. 24, Dec. 15, 2004, pp. 8442-8450.

Paez et al., "EGFR Mutations in Lung Cancer: Correlation with Clinical Response to Gefitinib Therapy," Apr. 2004, Science, 304:1497-1500.

Pham et al., "Use of Cigarette-Smoking History to Estimate the Likelihood of Mutations in Epidermal Growth Factor Receptor Gene Exons 19 and 21 in Lung Adenocarcinomas," Apr. 2006, Journal of Clinical Oncology, 24:1700-1704.

Rahman et al., "Electrochemical sensors based on organic conjugated polymers", Sensors, (20080000), vol. 8, pp. 118-141, XP055241017.

Sequist et al., "Molecular Predictors of Response to Epidermal Growth Factor Receptor Antagonists in Non-Small-Cell Lung Cancer," Feb. 2007, Journal of Clinical Oncology, 25:587-595.

Sharma et al., "Epidermal growth factor receptor mutations in lung cancer," Mar. 2007, Nature Reviews Cancer, 7(3):169-181.

Wei et al., "Noninvasive saliva-based EGFR gene mutation detection in patients with lung cancer," Nov. 2014, American Journal of Respiratory and Critical Care Medicine, 190(10):1117-1126.

Wei et al., "Serum creatinine detection by a conducting-polymer-based electrochemical sensor to identify allograft dysfunction", Analytical Chemistry, (20120000), vol. 84, pp. 7933-7937, XP055241019.

Yap et al., "Intratumor Heterogeneity: Seeing the Wood for the Trees," Mar. 2012, Science Translational Medicine, 4 (127)127ps10.

Zang et al., "Comparison of EGFR Signaling Pathway Somatic DNA Mutations Derived From Peripheral Blood and Corresponding Tumor Tissue of Patients with Advanced Non-Small-Cell Lung Cancer Using Liquidchip Technology," Nov. 2013, The Journal of Molecular Diagnostics, 15(6):819-826.

* cited by examiner

NON-INVASIVE GENE MUTATION DETECTION IN LUNG CANCER PATIENTS

CROSS-REFERENCE TO RELATED APPLICATIONS

This application is a Continuation of U.S. patent application Ser. No. 15/313,301, filed Nov. 22, 2016, which is the U.S. national phase application filed under 35 U.S.C. § 371 claiming benefit to International Patent Application No. PCT/US15/034028, filed Jun. 3, 2015, which is entitled to priority under 35 U.S.C. § 119(e) to U.S. Provisional Patent Application No. 62/007,286, filed Jun. 3, 2014, each of which application is hereby incorporated herein by reference in its entirety.

STATEMENT REGARDING FEDERALLY SPONSORED RESEARCH OR DEVELOPMENT

This invention was made with Government support under TR00124, awarded by the National Institutes of Health. The Government has certain rights in the invention.

REFERENCE TO A "SEQUENCE LISTING," A TABLE, OR A COMPUTER PROGRAM LISTING APPENDIX SUBMITTED AS AN XML FILE

The Sequence Listing written in the XML file: "206030-0045-01US_SequenceListing.xml"; created on Dec. 2, 2022, and 6,192 bytes in size, is hereby incorporated by reference.

BACKGROUND OF THE INVENTION

Lung cancer has the highest incidence of all cancers and is the leading cause of cancer-related deaths worldwide, accounting for 29% of all male and 26% of all female cancer deaths (Siegel R, Naishadham D, Jemal A. Cancer statistics, 2012. *CA Cancer J Chn* 2012; 62: 10-29). Recent understanding of the pathogenesis and molecular oncology of lung cancers has contributed to the discovery of the biological and therapeutic importance of acquired genetic alterations in epidermal growth factor receptor (EGFR), which encodes a pharmacologically targetable tyrosine kinase (Lynch T J, Bell D W, Sordella R, et al. Activating mutations in the epidermal growth factor receptor underlying responsiveness of non-small-cell lung cancer to gefitinib. *The New England journal of medicine* 2004; 350: 2129-2139; Paez J G, Janne P A, Lee J C, et al. EGFR mutations in lung cancer: correlation with clinical response to gefitinib therapy. *Science* 2004; 304: 1497-1500). A deletion in exon 19 (p.E746_A750del) and a point mutation in exon 21 (p.L858R) occur most frequently and are associated with a high degree of responsiveness to EGFR tyrosine kinase inhibitors (TKIs). In 2009, the first randomized clinical trial (the Iressa Pan-Asia Study) demonstrated that, for advanced non-small-cell lung carcinoma (NSCLC) patients carrying an activating EGFR mutation, initial treatment with an EGFR-TKI was superior to standard platinum-based chemotherapy (Mok T S, Wu Y L, Thongprasert S, et al. Gefitinib or carboplatin-paclitaxel in pulmonary adenocarcinoma. *The New England journal of medicine* 2009; 361: 947-957). Subsequently, one single-arm study and three other randomized studies confirmed the association between activating EGFR mutations and objective response to gefitinib and/or erlotinib therapy (Maemondo M, Inoue A, Kobayashi K, et al. Gefitinib or chemotherapy for nonsmall-cell lung cancer with mutated EGFR. N Engl J Med 2010; 362: 2380-2388; Mitsudomi T, Morita S, Yatabe Y, et al. Gefitinib versus cisplatin plus docetaxel in patients with non-small-cell lung cancer harbouring mutations of the epidermal growth factor receptor (WJTOG3405): an open label, randomised phase 3 trial. *Lancet Oncol* 2010; 11: 121-128; Rosell R, Carcereny E, Gervais R, et al. Erlotinib versus standard chemotherapy as first-line treatment for European patients with advanced EGFR mutation-positive non-small-cell lung cancer (EURTAC): a multicentre, open-label, randomised phase 3 trial. *The lancet oncology* 2012; 13: 239-246; Zhou C, Wu Y L, Chen G, et al. Erlotinib versus chemotherapy as first-line treatment for patients with advanced EGFR mutation-positive non-small-cell lung cancer (OPTIMAL, CTONG-0802): a multicentre, open-label, randomised, phase 3 study. *Lancet Oncol* 2011; 12: 735-742).

EGFR mutation analysis is performed on tumor cells in biopsy or cytology specimens obtained from bronchoscopy, computed tomography (CT)-guided biopsy, surgical resection, or drainage from malignant pleural effusions. However, most NSCLC patients suffer from late-stage cancer and have to be subjected to the invasive biopsy procedure in order to provide tumor tissue for EGFR mutation testing. In addition, the progressive development of EGFR oncogene mutations eventually leads to drug resistance. Therefore, the initial detection and continuous monitoring of EGFR oncogenic mutations are important for the long-term management of NSCLC patients; this strategy enables clinicians to adjust therapeutic strategies, improving the clinical outcome of oncogene molecular targeted therapy.

Given that blood harbors the same genetic lesions as the primary tumor, blood-borne biomarkers such as circulating tumor cells (CTCs) and circulating tumor DNA are promising for the detection of somatic mutations derived from malignant tumors (Bidard F C, Weigelt B, Reis-Filho J S. Going with the flow: from circulating tumor cells to DNA. *Science translational medicine* 2013; 5: 207ps214). Since not all of the cells identified in blood are CTCs, nor are CTCs of all phenotypes captured by these approaches, it remains challenging to use CTCs to detect EGFR mutations (Wicha M S, Hayes D F. Circulating tumor cells: not all detected cells are bad and not all bad cells are detected. *Journal of clinical oncology: official journal of the American Society of Clinical Oncology* 2011; 29: 1508-1511). DNA extraction from plasma samples is relatively straightforward compared to CTC collection. However, detecting circulating tumor DNA in plasma requires the use of molecular methods such as polymerase chain reaction (PCR)-based technology (Kimura H, Kasahara K, Kawaishi M, et al. Detection of epidermal growth factor receptor mutations in serum as a predictor of the response to gefitinib in patients with non-small-cell lung cancer. *Clinical cancer research: an official journal of the American Association for Cancer Research* 2006; 12: 3915-3921; Kimura H, Suminoe M, Kasahara K, et al. Evaluation of epidermal growth factor receptor mutation status in serum DNA as a predictor of response to gefitinib (IRESSA). *British journal of cancer* 2007; 97: 778-784), high-performance liquid chromatography (Bai H, Mao L, Wang H S, et al. Epidermal growth factor receptor mutations in plasma DNA samples predict tumor response in Chinese patients with stages IIIB to IV non-small-cell lung cancer. *Journal of clinical oncology: official journal of the American Society of Clinical Oncology* 2009; 27: 2653-2659), and mutant-enriched liquid chips (Zhang H, Liu D, Li S, et al. Comparison of EGFR signaling pathway somatic DNA mutations derived from peripheral blood and corresponding tumor tissue of patients with advanced non-small-cell lung cancer using liquid chip technology. *The Journal of molecular diagnostics: JMD* 2013; 15: 819-826). These techniques are complicated, technique-dependent, and time-consuming, and are therefore limited in clinical use.

Thus, there is a need in the art for a system and method for guiding treatments for lung cancer that are non-invasive, always available, minimal or no sample preparation, and provide immediate information on EGFR mutation status. The present invention satisfies this need.

SUMMARY OF THE INVENTION

In one aspect, the present invention provides a device for detecting lung cancer in a subject. The device comprises an array of units on a substrate, each unit comprising an electrode chip including a working electrode, a counter electrode, and a reference electrode. The working electrode of at least one unit is coated with a conducting polymer embedded or functionalized with a capture probe which binds to a first marker of lung cancer.

In one embodiment, the working electrode, counter electrode, and reference electrode are comprised of a conductive material. In one embodiment, the conducting polymer comprises pyrrole. In one embodiment, the conducting polymer is electropolymerized on the working electrode by applying a cyclic square-wave electric field to the device.

In one embodiment, the first marker of lung cancer is a nucleic acid. In one embodiment, the capture probe is a nucleic acid that hybridizes to a nucleic acid sequence encoding mutant EGFR in a sample. In one embodiment, the capture probe is a nucleic acid that hybridizes to a nucleic acid sequence encoding wild-type EGFR in a sample.

In one embodiment, the nucleic acid encoding mutant EGFR encodes a EGFR mutant selected from the group consisting of E746-A750 deletion mutant of EGFR and L858R point mutation of EGFR. In one embodiment, the capture probe comprises a nucleotide sequence selected from the group consisting of SEQ ID NO: 1 and SEQ ID NO: 3.

In one aspect, the present invention provides a method of detecting lung cancer in a subject. The method comprises obtaining a sample of the subject; mixing a first portion of the sample with a solution comprising a labeled detector probe; adding the mixture to a first electrode chip on a device, the electrode chip comprising a working electrode, a counter electrode, and a reference electrode; wherein the working electrode is coated with a conducting polymer embedded with a capture probe capable of binding to first marker associated with lung cancer in the sample; and measuring the current in the electrode chip, wherein a change in current is correlated to the presence of the first marker associated with lung cancer in the sample.

In one embodiment, the method further comprises applying a cyclic square-wave electric field to the electrode chip during the adding step.

In one embodiment, the first marker comprises a variable region comprising a nucleic acid sequence harboring a mutation associated with lung cancer, and at least one of the detector probe and capture probe hybridizes to the variable region.

In one embodiment, the first marker associated with lung cancer comprises a nucleic acid encoding mutant EGFR. In one embodiment, the nucleic acid encoding mutant EGFR encodes a EGFR mutant selected from the group consisting of E746-A750 deletion mutant of EGFR and L858R point mutation of EGFR.

In one embodiment, the capture probe comprises a nucleotide sequence selected from the group consisting of SEQ ID NO: 1 and SEQ ID NO: 3.

In one embodiment, the labeled detector probe comprises a nucleotide sequence selected from the group consisting of SEQ ID NO: 2 and SEQ ID NO: 4.

In one embodiment, the sample is a saliva sample. In one embodiment, the sample is a blood sample.

In one aspect, the present invention provides a system for detecting lung cancer in a subject. The system comprises an electrochemical sensor chip having at least one well, wherein the at least one well contains a working electrode coated with a conducting polymer functionalized with at least one capture probe; and at least one labeled detector probe. In one embodiment, when the at least one labeled detector probe is mixed with a sample from the subject containing a first marker of lung cancer and added to the at least one well, an electric current is applied to the sample in the at least one well, such that when at least some of the first marker binds to the capture probe, a measurable change in electric current in the sample is created that is indicative of lung cancer.

In one embodiment, the first marker comprises a variable region comprising a nucleic acid sequence harboring a mutation associated with lung cancer, and at least one of the detector probe and capture probe hybridizes to the variable region. In one embodiment, the first marker is a nucleic acid encoding mutant EGFR.

In one embodiment, the change in current in the sample is measurable within 10 minutes after the sample has been loaded into the well.

In one embodiment, the nucleic acid encoding mutant EGFR encodes a EGFR mutant selected from the group consisting of E746-A750 deletion mutant of EGFR and L858R point mutation of EGFR.

In one embodiment, the capture probe comprises a nucleotide sequence selected from the group consisting of SEQ ID NO: 1 and SEQ ID NO: 3. In one embodiment, the labeled detector probe comprises a nucleotide sequence selected from the group consisting of SEQ ID NO: 2 and SEQ ID NO: 4.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2, comprising

FIG. 3, comprising (FIG. 3A) Design of the tumor burden study using EGFR L858R xenografted mice. Testing of the four groups of mice with (FIG. 3B) 10 μL of plasma (R=0.86), (FIG. 3C) 20 μL of plasma (R=0.98), and (FIG. 3D) 40 μL of plasma (R=0.95). Reactions were performed in triplicate with both the mean and standard deviations provided. Linear fits to the data appear in red with the correlation co-efficient R provided. Amperometirc current readout are listed in (FIG. 3E) with 10 μl of plasma, (FIG. 3F) 20 μl of plasma and (FIG. 3G) 40 μl of plasma.

FIG. 4, comprising

The platform was compared with biopsy determined EGFR mutation type directly in plasma and saliva from lung cancer patients. To detect the specific mutation type, corresponding probes were applied to the electrochemical sensor to detect the specific mutation type. (FIG. 4A) The probe for exon 19 deletion in saliva; (FIG. 4B) the probe for L858R in saliva; (FIG. 4C) the probe for exon 19 deletion in plasma; and (FIG. 4D) the probe for L858R in plasma. (***P<0.0001, one-way analysis of variance and Bonferroni post hoc test). (FIG. 4E) Amperometric current results with the probe for exon 19 deletion in saliva from patients with lung cancer.

FIG. 5, comprising (FIG. 5C) Receiver operating characteristic curves for detecting (left to right) the Exon 19 deletion (AUC=0.94, 95% CI, 0.82 to land the L858R mutation, respectively (AUC=0.96, 95% CI, 0.90-1).

FIG. 6, comprising

FIG. 7, comprising

DETAILED DESCRIPTION

Figure 1:
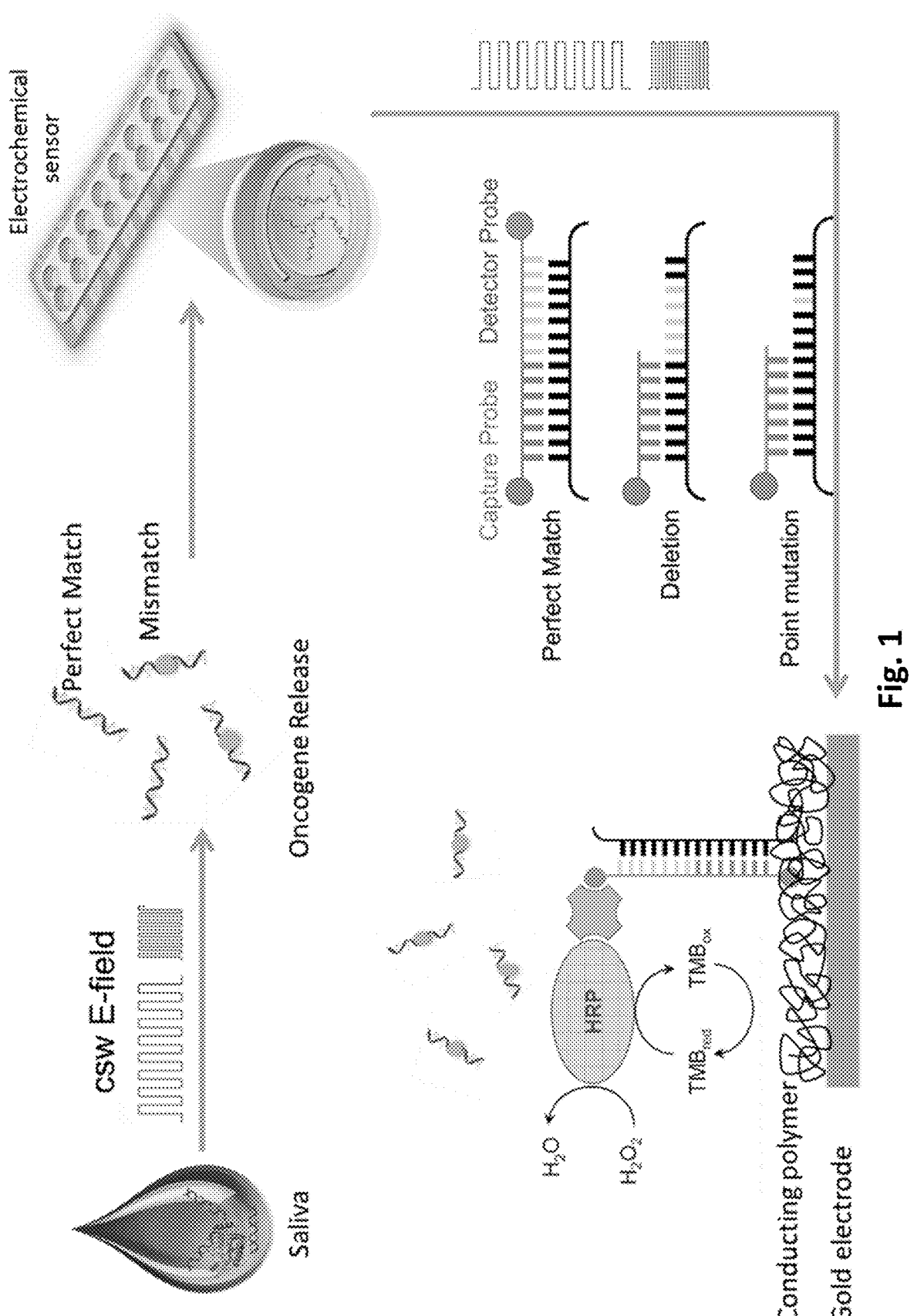
FIG. 1 is a schematic of the system platform array technology for the detection of EGFR mutations in the body fluids of lung-cancer patients. The cyclic-square wave of electrical field (csw E-field) was applied to release and detect the EGFR mutation. EGFR sequences were measured on the electrochemical sensor with pre-coated capture probe in conducting polymer. The horseradish peroxidase (HRP) labeled reporter probe generated amperometric signal when reaction with TMB (3,3',5,5'-tetramethylbenzidine) substrate under −200 mV electrical field.

It is to be understood that the figures and descriptions of the present invention have been simplified to illustrate elements that are relevant for a clear understanding of the present invention, while eliminating, for the purpose of clarity, many other elements found in typical biomarker detection systems and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein the terms "alteration," "defect," "variation," or "mutation," refers to a mutation in a gene in a cell that affects the function, activity, expression (transcription or translation) or conformation of the polypeptide that it encodes. Mutations encompassed by the present invention can be any mutation of a gene in a cell that results in the enhancement or disruption of the function, activity, expression or conformation of the encoded polypeptide, including the complete absence of expression of the encoded protein and can include, for example, missense and nonsense mutations, insertions, deletions, frameshifts and premature terminations. Without being so limited, mutations encompassed by the present invention may alter splicing the mRNA (splice site mutation) or cause a shift in the reading frame (frameshift).

The term "amplification" refers to the operation by which the number of copies of a target nucleotide sequence present in a sample is multiplied.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

As used herein, the term "marker" or "biomarker" is meant to include a parameter which is useful according to this invention for determining the presence and/or severity of lung cancer.

The level of a marker or biomarker "significantly" differs from the level of the marker or biomarker in a reference sample if the level of the marker in a sample from the patient differs from the level in a sample from the reference subject by an amount greater than the standard error of the assay employed to assess the marker, and preferably at least 10%, and more preferably 25%, 50%, 75%, or 100%.

The term "control or reference standard" describes a material comprising none, or a normal, low, or high level of one of more of the marker (or biomarker) expression products of one or more the markers (or biomarkers) of the invention, such that the control or reference standard may serve as a comparator against which a sample can be compared.

By the phrase "determining the level of marker (or biomarker) expression" is meant an assessment of the degree of expression of a marker in a sample at the nucleic acid or protein level, using technology available to the skilled artisan to detect a sufficient portion of any marker expression product.

"Differentially increased expression" or "up regulation" refers to biomarker product levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold higher or more, and any and all whole or partial increments therebetween than a control.

"Differentially decreased expression" or "down regulation" refers to biomarker product levels which are at least 10% or more, for example, 20%, 30%, 40%, or 50%, 60%, 70%, 80%, 90% lower or less, and/or 2.0 fold, 1.8 fold, 1.6 fold, 1.4 fold, 1.2 fold, 1.1 fold or less lower, and any and all whole or partial increments therebetween than a control.

A "disease" is a state of health of an animal wherein the animal cannot maintain homeostasis, and wherein if the disease is not ameliorated then the animal's health continues to deteriorate.

As used herein, an "instructional material" includes a publication, a recording, a diagram, or any other medium of expression which can be used to communicate the usefulness of a component of the invention in a kit for detecting biomarkers disclosed herein. The instructional material of the kit of the invention can, for example, be affixed to a container which contains the component of the invention or be shipped together with a container which contains the component. Alternatively, the instructional material can be shipped separately from the container with the intention that the instructional material and the component be used cooperatively by the recipient.

The term "label" when used herein refers to a detectable compound or composition that is conjugated directly or indirectly to a probe to generate a "labeled" probe. The label may be detectable by itself (e.g. radioisotope labels or fluorescent labels) or, in the case of an enzymatic label, may catalyze chemical alteration of a substrate compound or composition that is detectable (e.g., avidin-biotin). In some instances, primers can be labeled to detect a PCR product.

The "level" of one or more biomarkers means the absolute or relative amount or concentration of the biomarker in the sample.

The term "marker (or biomarker) expression" as used herein, encompasses the transcription, translation, post-translation modification, and phenotypic manifestation of a gene, including all aspects of the transformation of information encoded in a gene into RNA or protein.

By way of non-limiting example, marker expression includes transcription into messenger RNA (mRNA) and translation into protein, as well as transcription into types of RNA such as transfer RNA (tRNA) and ribosomal RNA (rRNA) that are not translated into protein.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "providing a prognosis" refers to providing a prediction of the probable course and outcome of lung cancer, including prediction of severity, duration, chances of recovery, etc. The methods can also be used to devise a suitable therapeutic plan, e.g., by indicating whether or not the condition is still at an early stage or if the condition has advanced to a stage where aggressive therapy would be ineffective.

A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype.

"Sample" or "biological sample" as used herein means a biological material isolated from an individual. The biological sample may contain any biological material suitable for detecting the desired biomarkers, and may comprise cellular and/or non-cellular material obtained from the individual.

"Standard control value" as used herein refers to a predetermined amount of a particular protein or nucleic acid that is detectable in a sample, such as a saliva sample, either in whole saliva or in saliva supernatant. The standard control value is suitable for the use of a method of the present invention, in order for comparing the amount of a protein or nucleic acid of interest that is present in a saliva sample. An established sample serving as a standard control provides an average amount of the protein or nucleic acid of interest in the saliva that is typical for an average, healthy person of reasonably matched background, e.g., gender, age, ethnicity, and medical history. A standard control value may vary depending on the protein or nucleic acid of interest and the nature of the sample (e.g., whole saliva or supernatant).

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

Description

The present invention relates to a rapid and accurate polymer-based electrochemical platform array for single or multi-biomarker detection from a biological sample, such as a saliva sample or blood sample, that are indicative of lung cancer. While the present invention is described generally for the testing of a saliva sample or blood sample, it should be appreciated that any biological fluid sample may be used, or even other tissue types, provided such alternative sample types carry the targeted markers to be analyzed. Non-limiting examples of such markers include all saliva-based lung cancer gene mutations, such as one or more mutations in epidermal growth factor receptor (EGFR), or any other markers associated with or indicative of lung cancer. For example, non-limiting examples of such detectable nucleic acids, or detectible mutations in genes include those associated with KRAS, BRAF, CCNI, FGF19, FRS2, GREB1 and LZTS1. It should be appreciated that any number of biomarkers can be integrated to the assay platform, including, without limitation, 1, 2, 4, 8, 16, 32 or 64 biomarkers per array.

The noninvasive detection of lung cancer in a subject via the present invention enables clinicians to identify the presence of lung cancer in a fast, economical and noninvasive manner. As contemplated herein, the present invention includes a multiplexing electrochemical sensor for detecting lung cancer biomarkers. The device utilizes a small sample volume with high accuracy. In addition, multiple markers can be measured simultaneously on the device with single sample loading. The device may significantly reduce the cost to the health care system, by decreasing the burden of patients returning to clinics and laboratories.

In one embodiment, the electrochemical sensor is an array of electrode chips (GeneFluidics, USA). As shown in FIG. 1, each unit of the array has a working electrode, a counter electrode, and a reference electrode. The three electrodes may be constructed of bare gold or other conductive material before the reaction, such that the specimens may be immobilized on the working electrode. Electrochemical current can be measured between the working electrode and counter electrode under the potential between the working electrode and the reference electrode. The potential profile can be a constant value, a linear sweep, or a cyclic square wave, for example. An array of plastic wells may be used to separate each three-electrode set, which helps avoid the cross contamination between different sensors. A conducting polymer may also be deposited on the working electrodes as a supporting film, and in some embodiments, as a surface to functionalize the working electrode. As contemplated herein, any conductive polymer may be used, such as polypyrroles, polanilines, polyacetylenes, polyphenylenevinylenes, polythiophenes and the like.

In a preferred embodiment, a cyclic square wave electric field is generated across the electrode within the sample well. In certain embodiments, the square wave electric field is generated to aid in polymerization of one or more capture probes to the polymer of the sensor. In certain embodiments, the square wave electric field is generated to aid in the hybridization of the capture probes with the marker and/or detector probe. The positive potential in the csw E-field helps the molecules accumulate onto the working electrode, while the negative potential removes the weak nonspecific binding, to generate enhanced specificity. Further, the flapping between positive and negative potential across the cyclic square wave also provides superior mixing during incubation, without disruption of the desired specific binding, which accelerates the binding process and results in a faster test or assay time. In one embodiment, a square wave cycle may consist of a longer low voltage period and a shorter high voltage period, to enhance binding partner hybridization within the sample. While there is no limitation to the actual time periods selected, examples include 0.15 to 60 second low voltage periods and 0.1 to 60 second high voltage periods. In a preferred embodiment, each square-wave cycle consists of 1 s at low voltage and 1 s at high voltage. For hybridization, the low voltage may be around −200 mV and the high voltage may be around +500 mV. In some embodiments, the total number of square wave cycles may be between 2-50. In a preferred embodiment, 5 cyclic square-waves are applied for each surface reaction. With the csw E-field, both the polymerization and hybridization are finished on the same chip within minutes. In some embodiments, the total detection time from sample loading is less than 30 minutes. In other embodiments, the total detection time from sample loading is less than 20 minutes. In other embodiments, the total detection time from sample loading is less than 10 minutes. In other embodiments, the total detection time from sample loading is less than 5 minutes. In other embodiments, the total detection time from sample loading is less than 2 minutes. In other embodiments, the total detection time from sample loading is less than 1 minute.

A multi-channel electrochemical reader (GeneFluidics) controls the electrical field applied onto the array sensors and reports the amperometric current simultaneously. In practice, solutions can be loaded onto the entire area of the three-electrode region including the working, counter, and reference electrodes, which are confined and separated by the array of plastic wells. After each step, the electrochemical sensors can be rinsed with ultrapure water or other washing solution and then dried, such as under pure $N_2$. In some embodiments, the sensors are single use, disposable sensors. In other embodiment, the sensors are reusable.

In one embodiment, the present invention is based on the affinity between a capture probe and a detector probe, as shown in FIG. 1. As contemplated herein, the assay platform may be organized as any type of affinity binding assay or immunoassay as would be understood by those skilled in the art. In another embodiment, the present invention includes a single platform for multiple lung cancer biomarker measurements, instead of a single marker. Currently, there is no such technology or device available for this purpose. In another embodiment, the present invention creates tremendous efficiencies in that it is simple, rapid and robust. For example, only small sample volumes are needed (e.g., 10 µl) and less than 10 minutes run time are needed. Multiple marker levels may be provided by the device. By providing statistical analysis the user may have an estimate of their risk, and by utilizing available networking systems, the results can be quickly transmitted for review by a clinician for further assessment.

For example, paired probes (capture and detector) specific for a mutation can be designed, such as for a deletion mutation, or for a point mutation. In the example of FIG. 1 and the experimental presented herein, two sets of probes, one for a deletion mutation and one for a point mutation, are used. The detector probes can be labeled, such as with fluorescein isothiocyanate or any other label known in the art. The capture probe is first copolymerized onto the bare gold electrode by applying a cyclic square wave electric field. For example, for each cycle during copolymerization, the electric field can be set to +350 mV for 1 s and +950 mV for 1 s. In total, polymerization may proceed for 5 cycles of 10 s, or however long is deemed necessary.

After polymerization, the sensor chip can be rinsed and dried for subsequent sample measurement. Samples, such as a cell-culture medium, a blood sample or a saliva sample, can be mixed with the detector probes and transferred onto the electrodes. Hybridization is then carried out at low and high voltage cycles, such as −200 mV for 1 s and +500 mV for 1 s. The total hybridization time can be 5 cycles for 10 s, for example. Next, the label is detected based on the label type. For example, an anti-fluorescein antibody conjugated to horseradish peroxidase in casein-phosphate-buffered saline can be used, and the 3,3',5,5'-tetramethylbenzidine substrate for horseradish peroxidase can be loaded, and the amperometric signal measured.

Capture probes embedded in the conductive polymer or otherwise used to functionalize the working electrode surface, and detector probes mixed with the sample may be constructed according to any protocol known in the art for the generation of probes.

The capture probe or detector probe of the sensor may be any one of a nucleic acid, protein, small molecule, and the like, which specifically binds one or more of the markers of interest. For example, in a particular embodiment, the capture probe and detector probe are oligonucleotides or polynucleotides comprising a region that is substantially complementary to one or more nucleic acid markers of the invention. In one embodiment, the capture probe and detector probe comprise a region that is substantially complementary to each other. That is, in one embodiment, the capture probe comprises a region that is substantially complementary to a region of the detector probe. Methods for designing and formulating oligonucleotide probes are well-known in the art.

In one embodiment, the marker comprises a variable region, where the variable region may comprise a mutation, such as a deletion, substitution, point mutation, and the like, associated with the disease. In one embodiment, the capture probe is designed to hybridize to a conserved region of the nucleic acid marker (i.e. present in wild-type and mutant isoforms). In one embodiment, the detector probe is designed to hybridize to the nucleic acid sequence of the variable region having a disease-associated mutation of the marker, thereby detecting the mutation in the sample. In another embodiment, the detector probe is designed to hybridize to the nucleic acid sequence of the variable region having a wild-type or non-mutated sequence, thereby detecting the presence of the wildtype marker in the sample. In one embodiment, the capture probe is designed to hybridize to the wildtype or mutated variable region, while the detector probe is designed to hybridize to the conserved region.

For example, in one embodiment, the capture probe comprises a nucleotide sequence that is substantially complementary to a conserved region of a nucleic acid encoding EGFR. In one embodiment, the detector probe comprises a nucleotide sequence that is substantially complementary to a variable region of a nucleic acid encoding EGFR, where the variable region encodes the wild-type amino acid sequence of EGFR. In one embodiment, the detector probe comprises a nucleotide sequence that is substantially complementary to a variable region of a nucleic acid encoding EGFR, where the variable region encodes the disease-associated mutant sequence of EGFR. For example, in certain embodiments, the detector probe comprises a nucleotide sequence that is substantially complementary to a variable region of a nucleic acid encoding EGFR, where the variable region encodes the disease-associated deletion mutant or point mutation of EGFR.

In one embodiment, when the present invention is used for detecting a nucleic acid encoding the E746-A750 deletion mutant of EGFR, the capture probe comprises a nucleic acid molecule comprising the nucleotide sequence of SEQ ID NO: 1. In one embodiment, when the present invention is used for detecting a nucleic acid encoding the L858R point mutation of EGFR, the capture probe comprises a nucleic acid molecule comprising the nucleotide sequence of SEQ ID NO: 3.

In one embodiment, when the present invention is used for detecting a nucleic acid encoding the E746-A750 deletion mutant of EGFR, the detector probe comprises a nucleic acid molecule comprising the nucleotide sequence of SEQ ID NO: 2. In one embodiment, when the present invention is used for detecting a nucleic acid encoding the L858R point mutation of EGFR, the detector probe comprises a nucleic acid molecule comprising the nucleotide sequence of SEQ ID NO: 4.

In one embodiment, the detector probe comprises a detectable label which induces a change in current of the sensor, thereby indicating the hybridization of the detector probe, and associated marker, with the capture probe. In certain embodiments, the detectable label itself may be sufficient to alter the current of the sensor. In certain embodiments, the detectable label induces the change in current when it comes into contact with an exogenous reactant. For example, the detectable label may react with the reactant to produce a local change sensed by the electrodes of the sensor to produce an amperometric signal. Therefore, in certain embodiments, the reactant is added to the sensor prior, during, or after the application of the sample to the sensor.

In certain embodiments, the detectable label is directly conjugated to the detector probe. In another embodiment, the detectable label is bound to the detector probe via an intermediate tag or label of the probe. For example, in one embodiment, the detector probe comprises a tag, label, or epitope, which can be used to bind to an antibody or other binding compound harboring the detectable label described above.

Examples of detectable labels and reactants to produce a local change in an electrochemical sensor are well known in the art. In one embodiment, the detectable label comprises HRP and the reactant is TMB, which react to generate an amperometric signal. In another embodiment, the detectable label comprises urease, while the reactant comprises urea.

There is no limitation to the concentrations of such probes used, and may be optimized as needed by the user.

Due to the enhanced sensitivity of the present invention, very small volumes may be used to perform the desired assays. For example, the biological sample size from the subject may be between 5-100 microliters. In a preferred embodiment, the sample size need only be about 40 microliters. There is no limitation to the actual or final sample size to be tested.

The present invention also relates to a method of detecting one or more markers associated with or indicative of lung cancer in a subject. In one embodiment, the method may be performed as a hybridization assay and includes the steps of obtaining a sample from the subject, adding an detector probe labeled with a detectable moiety directed against a targeted marker of lung cancer to the sample, applying the sample to an electrode chip coated with a conducting polymer previously embedded or functionalized with the capture probe, and measuring the current in the electrode chip. The detectable moiety may be measured, or the magnitude of the current in the sample may be measured, to determine the presence or absence of the marker in the sample. In certain embodiments, hybridization of the marker to the electrode of the sensor results in an increase in current or negative current. For example, in one embodiment, hybridization results in a current in the range of about −10 nA to about −1000 nA.

The present invention provides a method for diagnosing lung cancer in a subject. Accordingly, the present invention features methods for identifying subjects who are at risk of developing lung cancer, including those subjects who are asymptomatic or only exhibit non-specific indicators of lung cancer by detection of the biomarkers disclosed herein. These biomarkers are also useful for monitoring subjects undergoing treatments and therapies for lung cancer, and for selecting or modifying therapies and treatments that would be efficacious in subjects having lung cancer, wherein selection and use of such treatments and therapies slow the progression of lung cancer, or prevent their onset.

In certain embodiments, the biomarkers detected by way of the system and method of the invention include, but are not limited to nucleic acids, or detectible mutations in genes including those associated with EGFR, KRAS, BRAF, CCNI, FGF19, FRS2, GREB1 and LZTS1. In certain embodiments, the nucleic acid biomarkers comprise one or more disease-associated mutations, including, insertions, deletions, substitutions, translocations, point mutations, single nucleotide variants (SNVs), and the like. The present invention may be used to detect any disease-associated biomarker or disease-associated mutation known in the art or discovered in the future. Exemplary mutations present in various forms of cancer may be found, for example, in the Catalogue of Somatic Mutations in Cancer (COSMIC) (Wellcome Trust Sanger Institute).

In certain embodiments, the biomarkers detected by way of the system and method of the present invention comprise mutant EGFR and nucleic acid molecules encoding mutant EGFR. For example, various EGFR mutants are associated with lung cancer, including but not limited deletions in exon 19, point mutations in exons 18-21, and in-frame insertions or duplications that occur mostly in exon 20.

Exemplary deletions in exon 19 include for example deletion of one or more amino acids in the region of K745-S752, including but not limited to, E746-A750 deletion, K745-E749 deletion, E746-E749 deletion, and E746-R748 deletion. Exemplary point mutations of EGFR include, but are not limited to G719X, L858R, T790M, and L861Q.

The present invention may be used to detect any such mutation, as the capture probe and/or detector probe may be specifically designed to hybridize to a nucleic acid molecule encoding the mutant protein of interest.

The invention provides improved diagnosis and prognosis of lung cancer. The risk of developing lung cancer can be assessed by measuring one or more of the biomarkers described herein, and comparing the measured values to reference or index values. Such a comparison can be undertaken with mathematical algorithms or formula in order to combine information from results of multiple individual biomarkers and other parameters into a single measurement or index. Subjects identified as having an increased risk of lung cancer can optionally be selected to receive treatment regimens, such as administration of prophylactic or therapeutic compounds or treatments to prevent, treat or delay the onset of lung cancer.

Identifying a subject before they develop lung cancer enables the selection and initiation of various therapeutic interventions or treatment regimens in order to delay, reduce or prevent the development or severity of the cancer. In certain instances, monitoring the levels of at least one biomarker also allows for the course of treatment of lung cancer to be monitored. For example, a sample can be provided from a subject undergoing treatment regimens or therapeutic interventions, e.g., drug treatments, radiation, chemotherapy, etc. for lung cancer. Samples can be obtained from the subject at various time points before, during, or after treatment.

The biomarkers of the present invention can thus be used to generate a biomarker profile or signature of subjects: (i) who do not have and are not expected to develop lung cancer and/or (ii) who have or expected to develop lung cancer. The biomarker profile of a subject can be compared to a predetermined or reference biomarker profile to diagnose or identify subjects at risk for developing lung cancer, to monitor the progression of disease, as well as the rate of progression of disease, and to monitor the effectiveness of lung cancer treatments. Data concerning the biomarkers of the present invention can also be combined or correlated with other data or test results for lung cancer, including but not limited to imaging data, medical history and any relevant family history.

The present invention also provides methods for identifying agents for treating lung cancer that are appropriate or otherwise customized for a specific subject. In this regard, a test sample from a subject, exposed to a therapeutic agent, drug, or other treatment regimen, can be taken and the level of one or more biomarkers can be determined. The level of one or more biomarkers can be compared to a sample derived from the subject before and after treatment, or can be compared to samples derived from one or more subjects who have shown improvements in risk factors as a result of such treatment or exposure.

In one embodiment, the invention is a method of diagnosing lung cancer. In one embodiment, the method includes determining the stage or severity of lung cancer. In some embodiments, these methods may utilize a biological sample (such as urine, saliva, blood, serum, plasma, amniotic fluid, or tears), for the detection of one or more markers of the invention in the sample. Frequently the sample will be a "clinical sample" which is a sample derived from a patient. In one embodiment, the biological sample is a blood sample. In certain embodiments, the biological sample is a serum sample or a plasma sample, derived from a blood sample of the subject.

In one embodiment, the method comprises detecting one or more markers in a biological sample of the subject. Preferably, the biological sample is saliva. In various embodiments, the level of one or more of markers of the invention in the biological sample of the subject is compared with the level of a corresponding biomarker in a comparator. Non-limiting examples of comparators include, but are not limited to, a negative control, a positive control, an expected normal background value of the subject, a historical normal background value of the subject, an expected normal background value of a population that the subject is a member of, or a historical normal background value of a population that the subject is a member of.

In another embodiment, the invention is a method of monitoring the progression of lung cancer in a subject by assessing the level of one or more of the markers of the invention in a biological sample of the subject.

In various embodiments, the subject is a human subject, and may be of any race, sex and Information obtained from the methods of the invention described herein can be used alone, or in combination with other information (e.g., disease status, disease history, vital signs, blood chemistry, etc.) from the subject or from the biological sample obtained from the subject.

In other various embodiments of the methods of the invention, the level of one or more markers of the invention is determined to be increased when the level of one or more of the markers of the invention is increased by at least 10%, by at least 20%, by at least 30%, by at least 40%, by at least 50%, by at least 60%, by at least 70%, by at least 80%, by at least 90%, or by at least 100%, when compared to with a comparator control.

In the methods of the invention, a biological sample from a subject is assessed for the level of one or more of the markers of the invention in the biological sample obtained from the patient. The level of one or more of the markers of the invention in the biological sample can be determined by assessing the amount of polypeptide of one or more of the biomarkers of the invention in the biological sample, the amount of mRNA of one or more of the biomarkers of the invention in the biological sample, the amount of DNA of one or biomarkers of the invention in the biological sample, the amount of enzymatic activity of one or more of the biomarkers of the invention in the biological sample, or a combination thereof.

The present invention further includes an assay kit containing the electrochemical sensor array and instructions for the set-up, performance, monitoring, and interpretation of the assays of the present invention. Optionally, the kit may include reagents for the detection of at least one of the biomarkers. The kit may also optionally include the sensor reader.

EXPERIMENTAL EXAMPLES

The invention is further described in detail by reference to the following experimental examples. These examples are provided for purposes of illustration only, and are not intended to be limiting unless so specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out exemplary embodiments of the present invention, and are not to be construed as limiting in any way the remainder of the disclosure.

Example 1 Noninvasive EGFR Gene Mutation Detection in Patients with Lung Cancer

The detection of EGFR mutations by the system of the present invention was developed and validated in four consecutive phases. First, in vitro spike-in experiments were carried out with human lung-cancer cell lines with two specific human EGFR mutations: c.2236_2250del15, which encodes the p.E746-A750 mutation (the major form of the exon 19 deletion) that is present in the HCC827 cell line, and c.2573T>G, which encodes the p.L858R mutation in the NCI-H1975 cancer cell line. Second, mutant EGFR DNA was detected in body fluids as a function of lung tumor burden in a mouse lung cancer xenograph model. Plasma from mice xenografted with the human lung cancer cell line NCI-H1975 (carrying the EGFR L858R mutation) was tested at various stages of tumor progression. Third, the system was used for the detection of EGFR mutations in saliva and plasma of NSCLC patients. Lastly, EGFR mutation detection was validated in saliva from human lung cancer patients in a blinded clinical study.

The materials and methods employed in these experiments are now described.

Cell Culture and DNA Isolation

Human lung cancer cell lines NCI-H1975 and HCC827 were obtained from the American Type Culture Collection (Manassas, Va., USA). Cells were propagated in RPMI-1640 medium with 10% fetal bovine serum. Genomic DNA was isolated with the DNeasy Blood & Tissue Kit (Qiagen, Valencia, CA, USA), and DNA concentration was determined using a Nanodrop™ 8000 spectrophotometer (Thermo Scientific, Wilmington, DE, USA).

Mouse Lung Cancer Xenograft Model

Female nu/nu mice ~6-8 weeks old were obtained from Charles River Labs (MA, USA). Animals were housed under standard clean-room conditions in accordance with the guidelines of the Pfizer Institutional Animal Care and Use Committee. NCI-H1975 cells ($2 \times 10^6$ cells) were re-suspended in serum-free Matrigel at a 1:1 ratio and immediately implanted subcutaneously in the right flank of each animal (n=9).

Patient Samples

To be eligible for inclusion in this study, patients were required to have pathology-confirmed stage III or IV lung adenocarcinoma. Patients treated at NCKUH (Tainan, Taiwan) from June 2012 to December 2013 were enrolled. This study was approved by the Research Ethics Committee of NCKUH. All patients provided informed consent to participate in this study and gave permission for the use of their tumor tissues and the collection of their saliva for EGFR mutation analysis.

To ensure blinding of the analysis during the validation phase, the center in charge of distribution (MD Anderson Cancer Center (Houston, TX)) assigned random numbers to saliva samples from NCKUH and distributed the codes to UCLA for testing. The person who assigned the random numbers at the distribution center was not the same person who performed the testing at UCLA, nor the person who collected the saliva at NCKUH, thus ensuring complete blinding of the samples. The code on the saliva was broken only after the UCLA lab submitted the data.

Collection of Mouse Plasma

To isolate plasma from mice, blood was collected when tumors were 100-300 mm³, 500-900 mm³, or >1000 mm³ at 11, 16, and 19 days post-transplantation. Three mice were sacrificed per group, including naïve control mice. Animals were placed under anesthesia (isoflurane-oxygen mixture) and blood was acquired via cardiac puncture. Approximately 1 mL of blood was collected in EDTA-containing Vacutainer tubes (BD Biosciences, San Jose, USA) and spun at 1900×g for 10 min at 4° C. The plasma supernatant was aspirated, transferred to a 1.5-mL microcentrifuge tube, and centrifuged at 16,000×g for 10 min at 4° C. to remove additional cellular debris. The plasma supernatant was aspirated and transferred to another microcentrifuge tube and stored at −80° C. until use.

PCR-Based Analysis of EGFR Mutations

Tumor tissue from lung tumors, metastatic sites, and malignant effusion cell blocks were obtained for EGFR mutation analysis. Tissue samples that consisted of >80% tumor content as determined via microscopy with hematoxylin and eosin staining were selected for the study. Pleural effusion fluid was collected and centrifuged at 250×g for 10 min at 4° C., and the cell pellet was frozen. Sample processing, from sampling to freezing, required <2 h (39). Genomic DNA was extracted from cell lysates or tumor paraffin blocks using the QIAamp DNA Mini Kit (Qiagen) and used in EGFR mutation analysis, as described previously (40).

Saliva Collection

Since the exon 19 deletion and the exon 21 L858R point mutation represent 90% of EGFR sensitizing mutations (Sharma S V, Bell D W, Settleman J, Haber D A. Epidermal growth factor receptor mutations in lung cancer. *Nature reviews Cancer* 2007; 7: 169-181; Sequist L V, Bell D W, Lynch T J, Haber D A. Molecular predictors of response to epidermal growth factor receptor antagonists in non-small-cell lung cancer. *Journal of clinical oncology: official journal of the American Society of Clinical Oncology* 2007; 25: 587-595), only patients confirmed to be wildtype or harboring these mutations were allowed to enroll in the study. Unstimulated whole saliva was collected and processed according to previously established protocols (Li Y, St John M A, Zhou X, et al. Salivary transcriptome diagnostics for oral cancer detection. *Clin Cancer Res* 2004; 10: 8442-8450). Briefly, saliva samples were kept on ice during collection and were then centrifuged at 2,600×g for 15 min at 4° C. The supernatant was removed from the pellet, treated with RNase inhibitor (Superase-In, Ambion Inc., Austin, Tex., USA), and stored at −80° C. prior to use.

Detection of EGFR Mutations in Body Fluids Via System Platform

FIG. 1 illustrates the core technology of the system of the present invention. The sensor is a conducting polymer-based electrochemical chip with an array of 16 bare-gold electrode chips (GeneFluidics, Los Angeles, USA). Each unit of the array has a working electrode, a counter electrode, and a reference electrode. The 16-channel electrochemical (EC) reader (GeneFluidics) controls the electrical field applied onto the 16 array sensors and simultaneously reports the amperometric current.

Paired probes (capture and detector; Sigma, St. Louis, USA) specific for the two TKI-sensitive mutations were designed for the platform as follows: capture probe for the exon 19 deletion, 5'-TGT TGC TTC CTT GAT AGC GAC G-3' (SEQ ID NO: 1); detector probe for the exon 19 deletion, 5'-GGA ATT TTA ACT TTC TCA CCT-3'(SEQ ID NO: 2); capture probe for the L858R point mutation: 5'-CAG TTT GGC CCG CCC AAA ATC-3'(SEQ ID NO: 3); detector probe for the L858R mutation: 5'-TTG ACA TGC TGC GGT GTT TTC A-3' (SEQ ID NO: 4). As used in these experiments, the detector probes were labeled with fluorescein isothiocyanate (FITC) at their 3' end. Twenty microliters of the capture probe (100 nM) were first copolymerized with pyrrole (Sigma) and 100 µL of 3 M KCl (Mettler Toledo, Columbus, USA) in 1× phosphate-buffered saline (pH 7.5; Invitrogen, Grand Island, USA) onto the bare gold electrode by applying a cyclic square wave electric field. KCl was added at a final concentration of 300 mM to achieve high ionic strength. For each cycle, the electric field was set to +350 mV for 1 s and +950 mV for 1 s. In total, polymerization proceeded for 5 cycles of 10 s.

After polymerization, the sensor chip was rinsed with deionized water and dried. Samples, such as cell-culture medium or 404, samples of blood or saliva, were then mixed with 5 μL of the detector probes in 955 μL Tris-HCl buffer (Invitrogen) and transferred onto the electrodes. Hybridization was carried out at −200 mV for 1 s and +500 mV for 1 s. The total polymerization time was again 5 cycles for 10 s. Next, 150 U/mL of anti-fluorescein antibody conjugated to horseradish peroxidase (1:1000 dilution; Roche, Indianapolis, USA) in casein-phosphate-buffered saline (Invitrogen) was added. Finally, the 3,3',5,5'-tetramethylbenzidine substrate for horseradish peroxidase was loaded, and the amperometric signal was measured. The total detection time was <10 min and required only 20-40 μL of biological sample.

Statistical Analysis

To evaluate the performance of the system of the present invention in detecting EGFR mutations, the receiver operating characteristic curve was plotted for each probe and the AUC was calculated and its 95% confidence interval. All analyses were performed using SAS 9.3 TS Level 1M1 (DeLong E R, DeLong D M, Clarke-Pearson D L. Comparing the areas under two or more correlated receiver operating characteristic curves: a nonparametric approach. *Biometrics* 1988; 44: 837-845).

The results of the experiments are now described

Optimization of EGFR Mutations Detection Using Lung-Cancer Cell Lines

The system as depicted in FIG. 1 was optimized to detect the following EGFR mutations: c.2573T>G in exon 21 (encoding p.L858R) and c.2236_2250del15 in exon 19 (coding for a 15-base pair deletion resulting in mutation E746-A750del). Genomic DNA samples from human lung-cancer cell lines NCI-H1975 and HCC827, harboring the respective mutations, were used for detection optimizations.

Figures 2A, 2B, 2C, 2D:
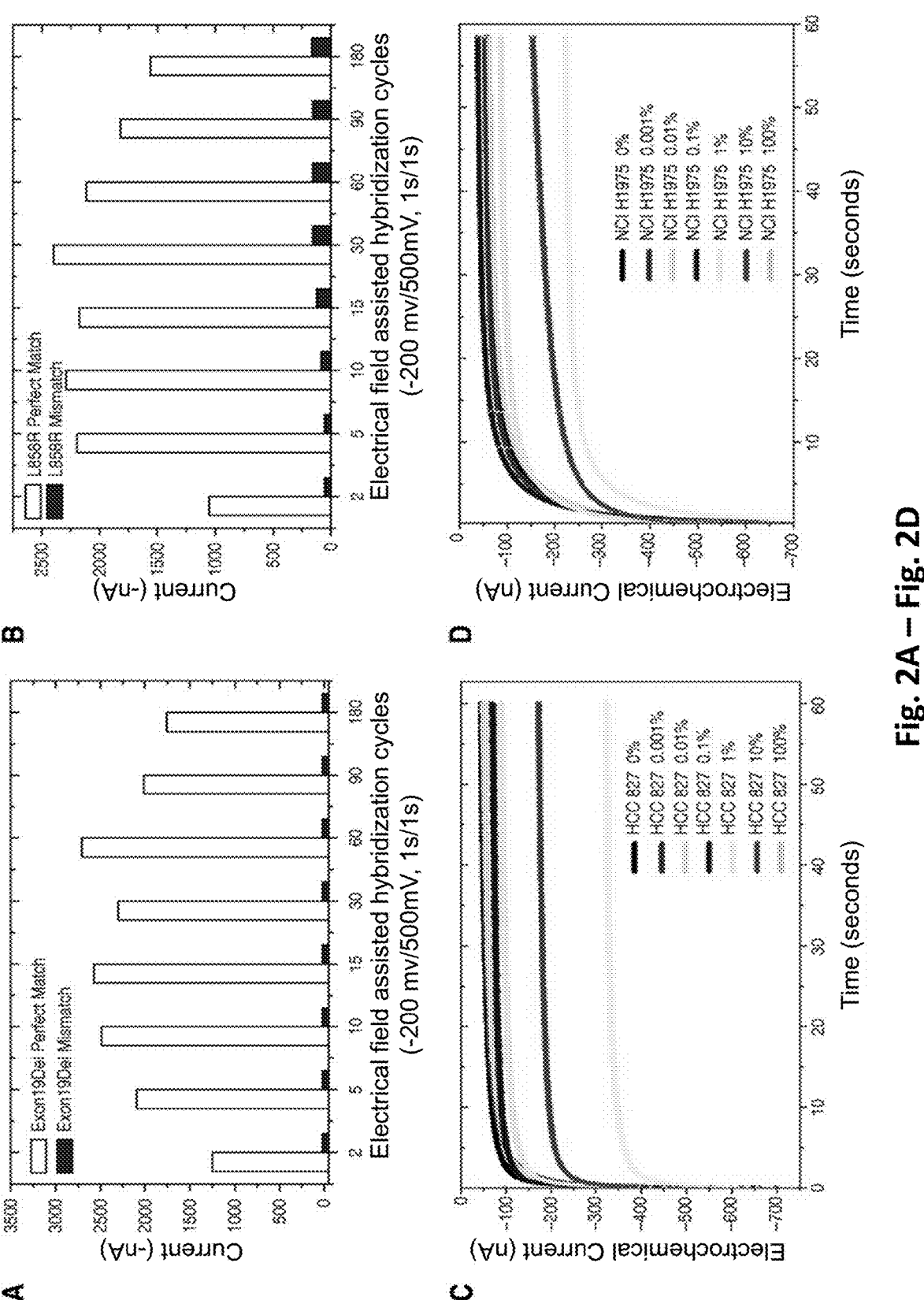
FIG. 2A through FIG. 2F, is a set of graphs depicting the in vitro optimization of the platform for specific human EGFR mutation detection. Cycle numbers for the application of EFIRM for the detection of oligos carrying the (FIG. 2A) exon 19 deletion and (FIG. 2B) the L858R mutation. Targeting oligos were dissolved in Tris-HCl buffer at a final concentration of 1 nM. Wild-type sequences were utilized as mismatch sequences. The TKI-sensitive EGFR mutations as Exon 19 deletion (taken from HCC827 cells) and L858R (taken from NCI-H1975 cells) were assayed by decreasing the ratio of targeted oncogene sequence to other sequences. Electrochemical current readouts are listed in (FIG. 2C) amperometric signals for Exon 19 deletion and (FIG. 2D) L858R. Reactions were performed in triplicate using 20 ng of input DNA. Mean and standard deviation from triplicates experiments are provided (FIG. 2E) for Exon 19 deletion and (FIG. 2F) L858R.
Figures 2E, 2F:
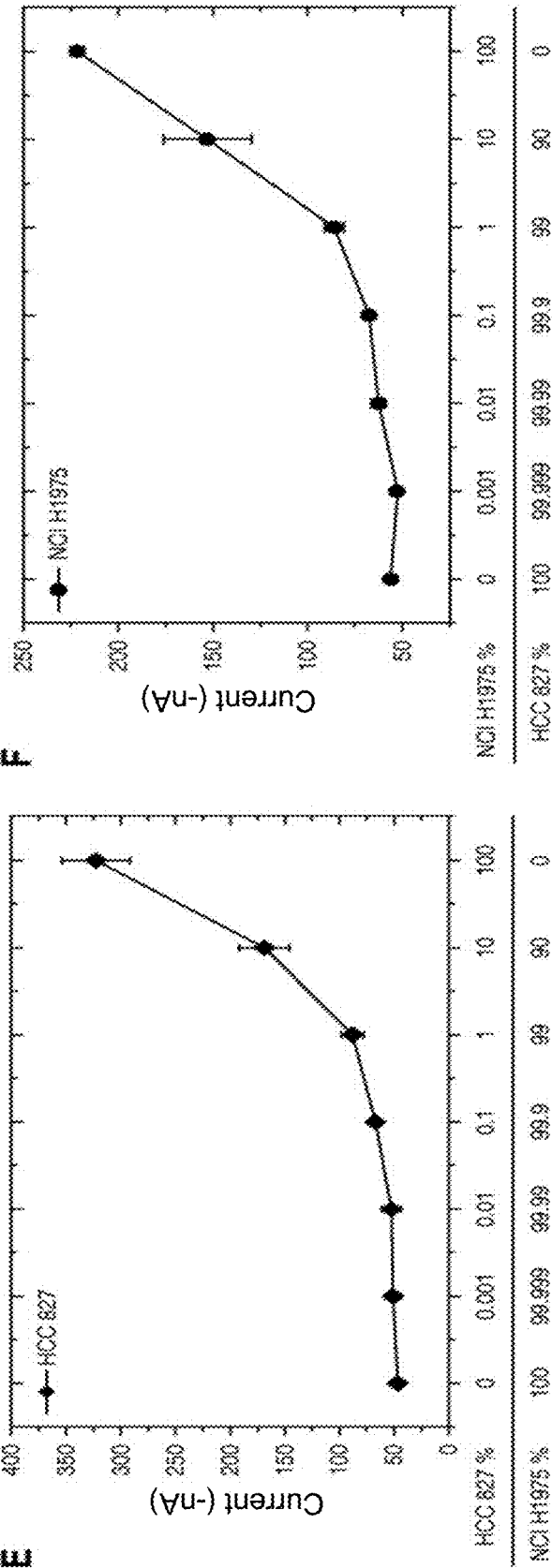

The electrical field profile was first optimized for the appropriate number of hybridization cycles (FIG. 2A and FIG. 2B). The hybridization signal increased rapidly after two cycles of electrical waves. After five cycles, the perfect match signal reached a plateau, while the mismatch sequences generated only background signal levels. Therefore, the optimized hybridization cycle was defined as five for all subsequent studies.

The specificity and sensitivity of the system for detecting the respective EGFR mutations were investigated by decreasing the ratio of mutant EGFR DNA to wild-type EGFR DNA (FIG. 2C-FIG. 2F). For the p.E746-A750del, as little as 0.1% mutant DNA was detected in the presence of wild-type DNA. For the p.L858R point mutation, as little as 1% mutant DNA was detected when a control sample was used. Ten microliters of 2 ng/μL DNA were used for these experiments. These data demonstrate that system of the present invention can detect EGFR mutations with high sensitivity and specificity.

Figures 3A, 3B, 3C, 3D:
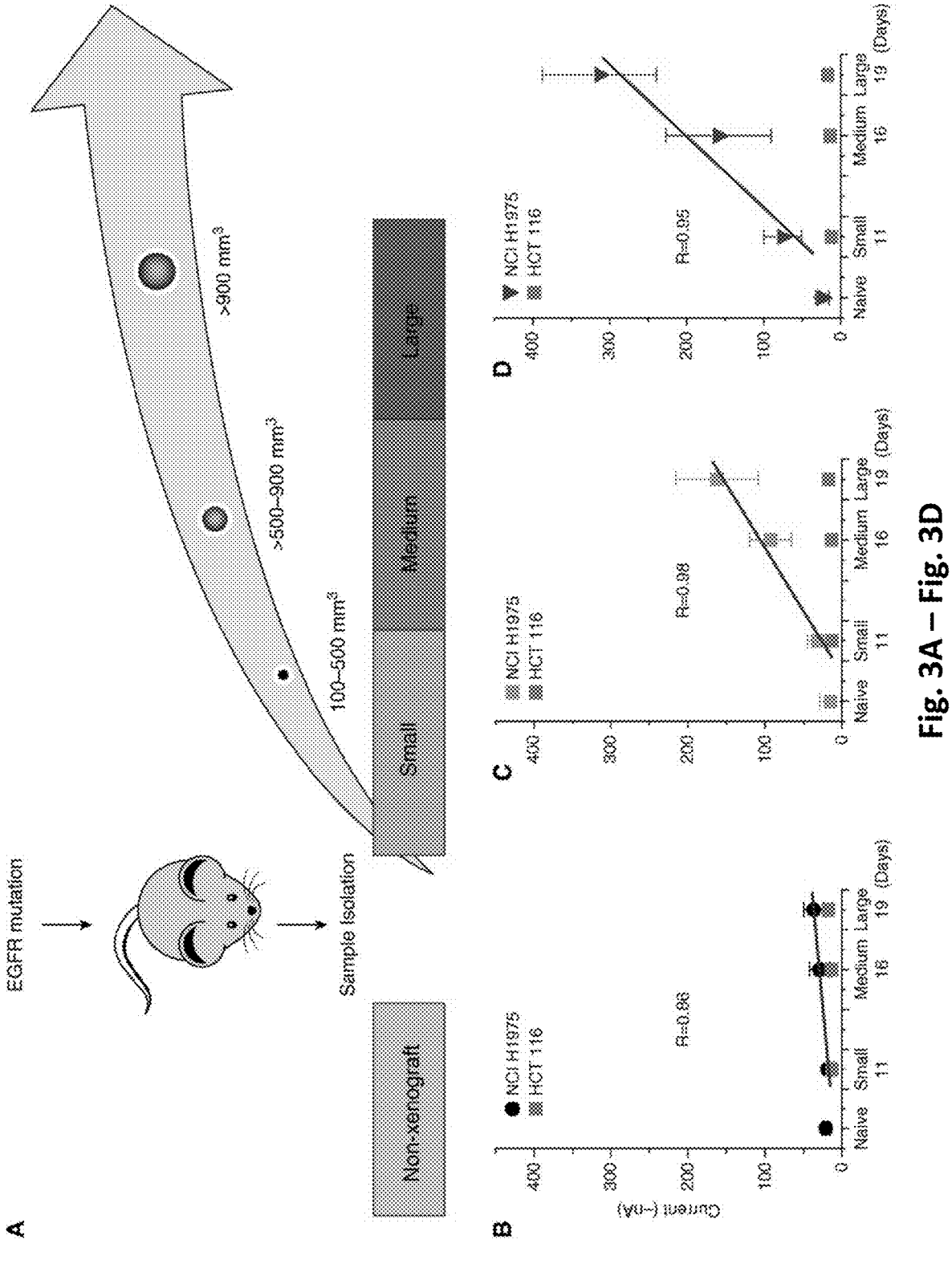
FIG. 3A through FIG. 3G, depicts the detection of EGFR L858R point mutation in xenografted lung cancer mice via the system of the present invention.
Figures 3E, 3F, 3G:
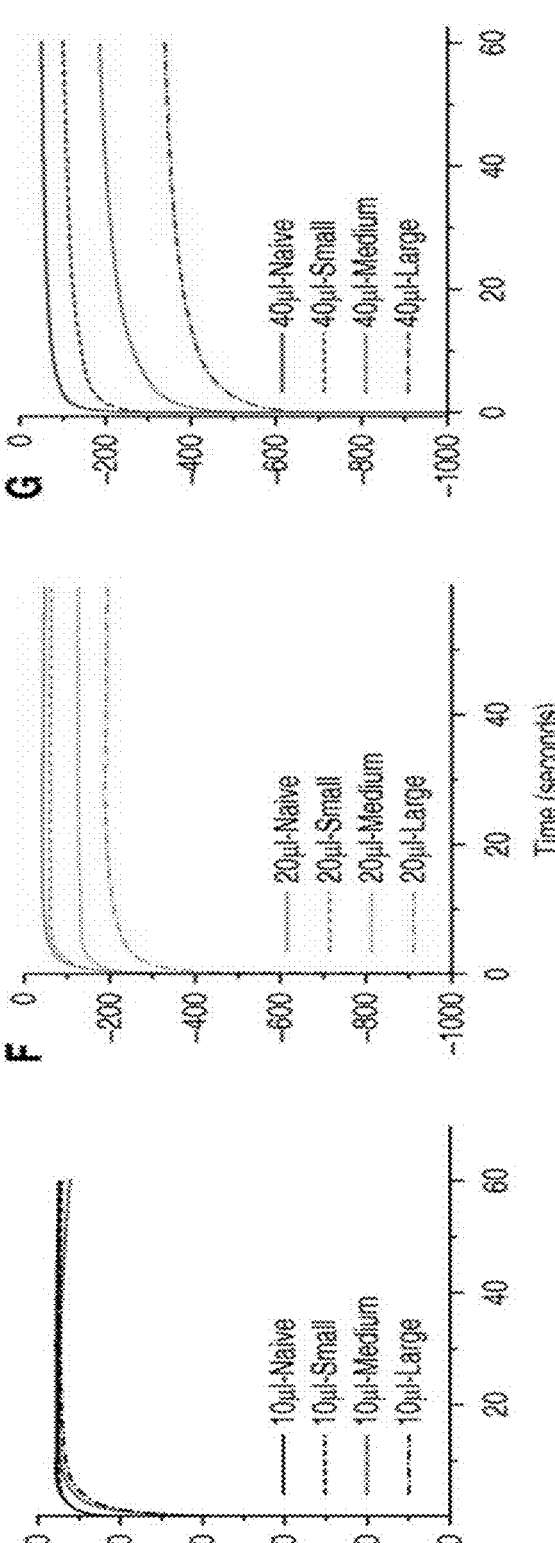

Detection of EGFR Mutation in Plasma of a Mouse Model with Xenografted Lung Cancer Plasma was banked from a mouse model xenografted with the human lung cancer cell line NCI-H1975 that harbors the EGFR point mutation p.L858R at increasing tumor burden in 4 different settings: (1) no tumor (non-xenograft mice), (2) small tumors (100-500 mm³), (3) medium tumors (500-900 mm³), and (4) large tumors (>900 mm³). Mice xenografted with the HCT 116 cell line, which carried the EGFR wild type, were used as a control (Bamford et al., 2004, Br J Cancer, 91: 355-358). To determine if the optimized system can detect the EGFR mutation in plasma of these xenografted mice, forty microliters of mouse plasma were assayed in triplicate with the system at defined time intervals of day 0, 11, 16 and 19 (FIG. 3A). A positive relationship between electrochemical current and tumor size was observed (FIG. 3B-FIG. 3D; (b) 10 μl of plasma (R=0.86), (c) 20 μl of plasma (R=0.98), and (d) 40 μl of plasma (R=0.95)). Increased plasma volume yielded better discrimination of different tumor sizes (FIG. 3B-FIG. 3D). Naïve mice were associated with the lowest amount of signal (FIG. 3B-FIG. 3D). Small tumors (100-500 mm³) were associated with signal levels that significantly differed from the naïve group, and larger tumors had higher current signals (FIG. 3B-FIG. 3D). After 19 days of growth, DNA from mice with large tumors generated electrochemical current on the order of several hundred nA (FIG. 3C and FIG. 3D). These results indicate that the system of the present invention can detect and monitor the progressive tumor development from the plasma of xenografted mice. Amperometric readouts are provided in FIG. 3E-FIG. 3G.

Detection of EGFR Mutations in Plasma and Saliva from NSCLC Patients Using the Platform Assay Experiments were conducted to examine whether the two most common TKI-sensitive EGFR mutations (p.L858R and p.E746-A750del) can be detected by the system of present invention in plasma and saliva of NSCLC patients. For each NSCLC subject, tissue, plasma and saliva were collected at National Cheng Kung University Hospital (NCKUH). After sample collection, biopsy-based EGFR genotyping was performed at NCKUH. plasma and saliva-based detection of the two EGFR mutations were assayed by EFIRM at University of California, Los Angeles (UCLA).

Figures 4A, 4B, 4C, 4D, 4E:
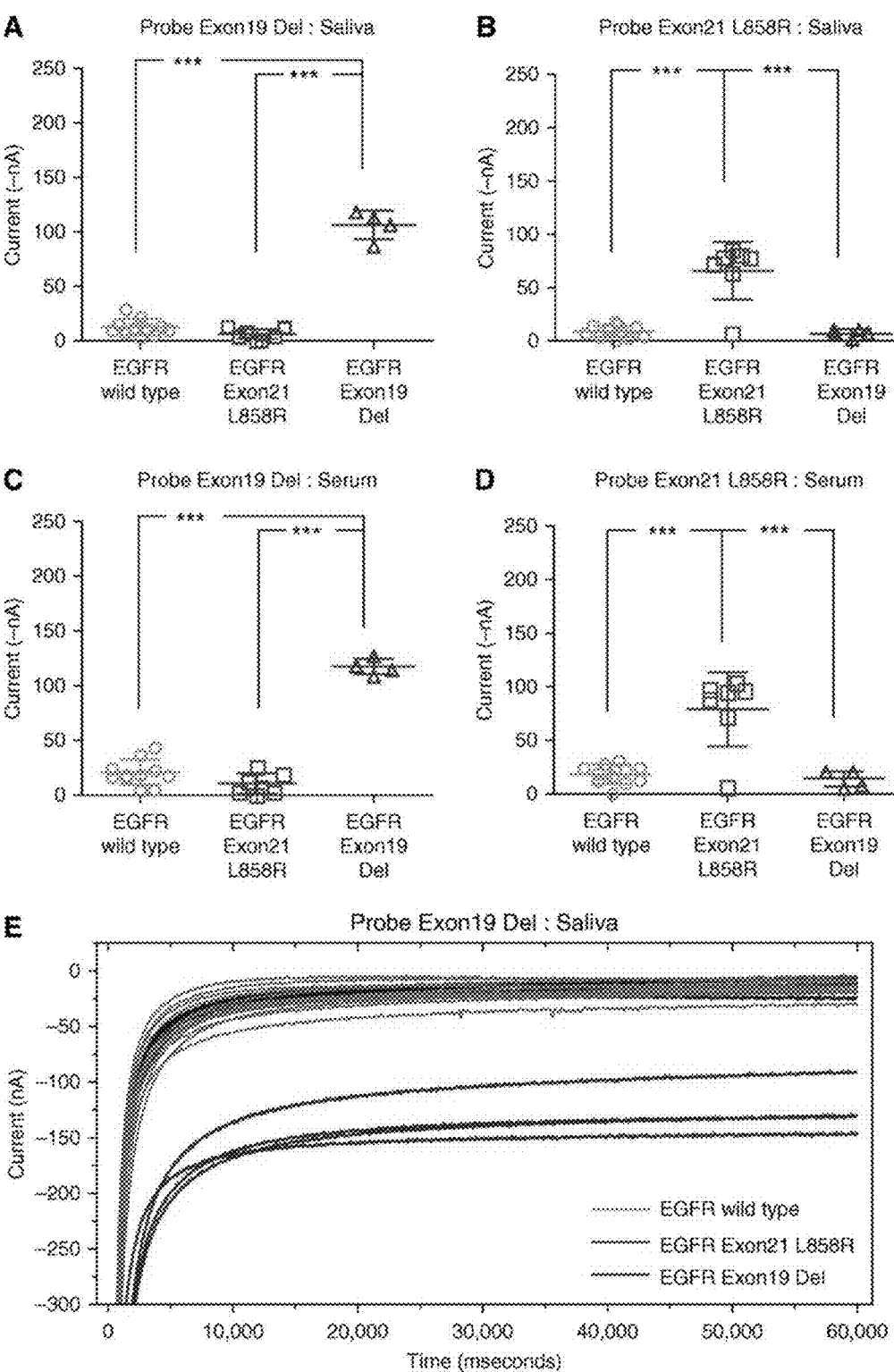
FIG. 4A through FIG. 4E, depicts the detection of EGFR mutations in plasma and saliva from NSCLC patients via the system of the present invention.

Twenty-two NSCLC patients (12 men and 10 women, mean age of 62.0±12.7, mostly non-smokers) met the enrollment criteria and were enrolled (Table 1). The EGFR mutation rate was comparable to other study in detecting EGFR mutation in Asia lung adenocarcinoma ranging from 38% (Huang Y S, Yang J J, Zhang X C, Yang X N, Huang Y J, Xu C R, Zhou Q, Wang Z, Su J, Wu Y L. Impact of smoking status and pathologic type on epidermal growth factor receptor mutations in lung cancer. *Chin Med J (Engl)* 2011; 124:2457-2460) to 55% (Ho H L, Chang F P, Ma H H, Liao L R, Chuang Y T, Chang-Chien Y C, Lin K Y, Chou T Y. Molecular diagnostic algorithm for epidermal growth factor receptor mutation detection in asian lung adenocarcinomas: Comprehensive analyses of 445 taiwanese patients with immunohistochemistry, per-direct sequencing and scorpion/ arms methods. *Respirology* 2013; 18:1261-1270). The plasma and saliva specimens were procured before the first treatment. FIG. 4 illustrates the results from saliva and plasma showing the respective EGFR mutation compared with biopsy-based genotyping. The original amperometric current signals from the detection of p.E746-A750del exon19 deletion group in saliva samples are shown in FIG. 4E, with data was read-out at 60 seconds. The amperometric currents of the exon 19 deletion group (p.E746-A750del) detected by EFIRM using an exon 19 probe were significantly higher than those in the wild-type and p.L858R mutant groups based on saliva (FIG. 4A and FIG. 4E; 106.3±13.2 in the p.E746-A750del group vs. 12.8±7.5 in the wild-type group and 6.3±4.7 in the p.L858R mutant group; P<0.0001). The amperometric currents of the exon 21 mutant group (p.L858R) detected by EFIRM using the L858R probe were significantly higher than those in the wild-type and p.L858R mutant groups (FIG. 4B; 66.5±27.2 in the p.L858R mutant group vs. 9.5±5.3 in the wild-type group and 7.7±4.2 in the p.E746-A750del group; P<0.0001). Similar results were obtained from plasma using the probe designed for the exon 19 deletion group (FIG. 4C; 117.2±8.1 in the p.E746-A750del group vs. 20.7±11.7 in the wild-type group and 10.4±9.2 in the p.L858R mutant group;

P<0.0001) and for the p.L858R mutant group (FIG. 4D; 79.0±34.2 in the p.L858R mutant group vs. 18.1±8.9 in the wild-type group and 13.5±7.4 in the p.E746-A750del group; P<0.0001). It is suggested that a cutoff at 2 SDs above the mean value from the control group to differentiate the mutant and control groups. These findings indicated that EFIRM could be used to detect specific EGFR mutations in the plasma and saliva of patients with NSCLC.

Blinded and Randomized Study to Detect EGFR Mutations in NSCLC Patients Using the Platform Assay To determine whether EGFR oncogenic mutations can be detected in the saliva of NSCLC patients using the optimized system technology, blinded saliva from 40 NSCLC patients harboring the two most common EGFR tyrosine kinase domain mutations (p.L858R and exon 19 deletion) and evaluated by the system of the present invention.

The forty saliva samples were obtained from patients with advanced NSCLC were collected at the National Cheng Kung University Hospital (NCKUH), blinded, tested, and sent to the University of California, Los Angeles (UCLA) for validation. Biopsy-based EGFR genotyping was performed at NCKUH (Table 2). The blinded samples were further randomized by a biostatistician from a third institution at MD Anderson Cancer Center (MDACC) followed by EFIRM measurements of the two EGFR mutations at UCLA. The platform assay was used to detect the two EGFR mutations in saliva of these patients at UCLA.

The patient cohort consisted of 22 men and 18 women, with a mean age of 58.8±10.4 years; 32 cases (80%) exhibited stage IV cancer and most patients were non-smokers (Table 1). The clinical characteristics, including tumor stage and EGFR mutations in the blinded group, were similar to those in the testing group.

Figures 5A, 5B, 5C:
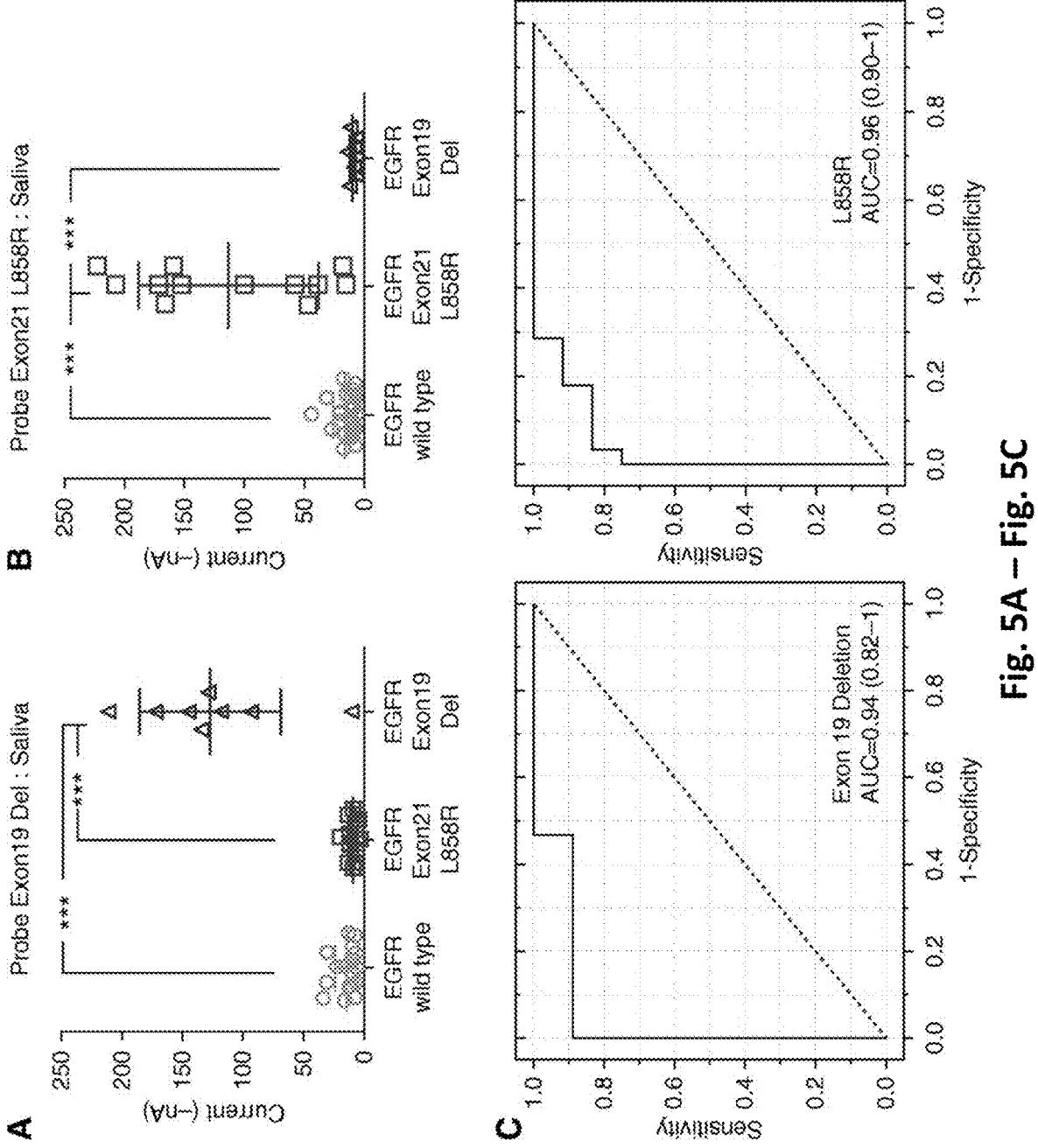
FIG. 5A through FIG. 5C, depicts the results of blinded and randomized clinical detection of EGFR mutations in saliva via the system of the present invention. EFIRM was carried out in duplicates. The absolute values of signal associated with (FIG. 5A) Exon19 deletion and (FIG. 5B) L858R point mutation according to patient subgroup are presented (***p<0.0001, one-way ANOVA and bonferroni post hoc test).
Figures 6A, 6B:
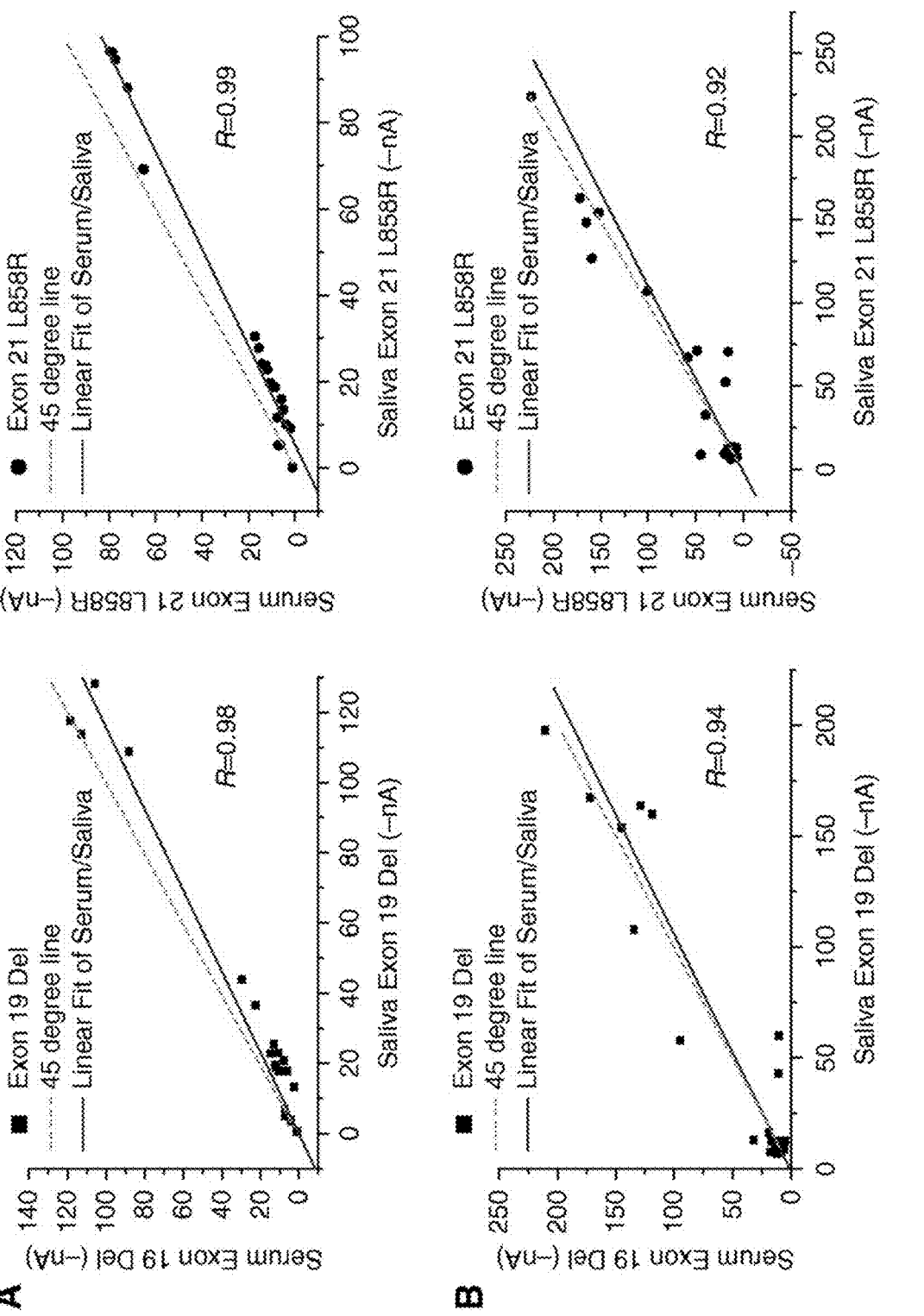
FIG. 6A and FIG. 6B, depicts the results of experiments demonstrating the correlation of EGFR mutation statuses between plasma and saliva using system of the present invention. The scattergram shows the correlation and linear regression between amperometric currents recorded using plasma and saliva. Each dot represents data for one patient in (FIG. 6A) the testing group and (FIG. 6B) the blinded group.

The amperometric currents of the exon 19 deletion group detected by EFIRM using an exon 19 probe were significantly higher than those in the wild-type and p.L858R mutant groups (FIG. 5A; 126.6±58.6 in the p.E746-A750del group vs. 14.5±3.5 in the wild-type group and 9.6±3.7 in the informative as plasma and serve as an additional bodily fluid for mutation testing. For the testing group, the amperometric currents of saliva were correlated with those from plasma using the two different probes (FIG. 6A; R=0.98, P<0.0001 in the p.E746-A750del groups and R=0.99, P<0.0001 in the p.L858R groups).

Figures 7A, 7B:
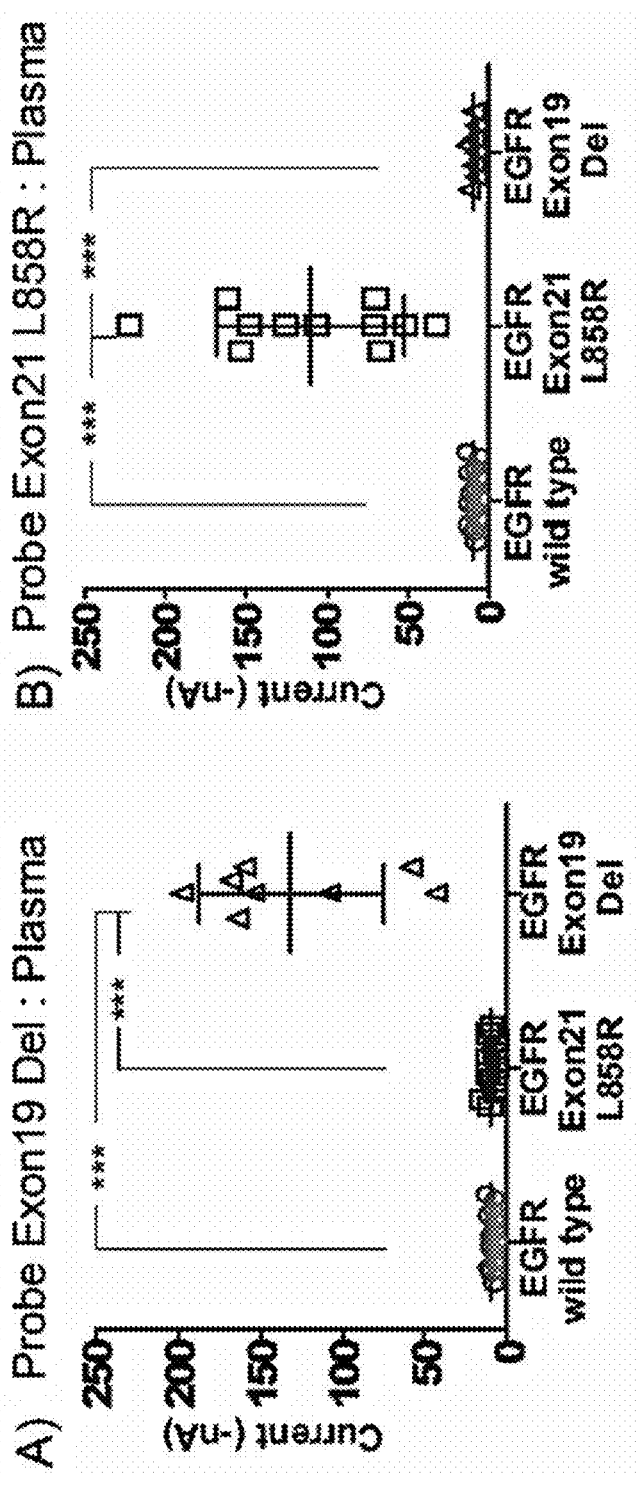
FIG. 7A and FIG. 7B, depicts the results of experiments demonstrating the detection of EGFR mutations from the plasma of 33 patients with NSCLC by using the system of the present invention. The amperometric currents of exon 19 deletion group that were detected using EFIRM with an exon 19 probe were significantly higher than those in the wild-type and p.L858R mutant groups (FIG. 7A: 131.3.6±55.76 in p.E746-A750del group versus 9.76±1.77 in wild-type group and 10.26±2.87 in the p.L858R mutant group, p<0.0001). Similar results were obtained using the probe for p.L858R (FIG. 7B: 110.6±57.99 in p.L858R mutant group versus 9.51±2.73 in wild-type group and 9.34±1.86 in p.E746-A750del group, p<0.0001).

Similar results were observed in the blinded group (33 plasma samples). It was first demonstrated that EFIRM could be used to detect specific EGFR mutations in the plasma of these 33 patients (FIG. 7A and FIG. 7B). As in the testing cohort, it was found that the amperometric currents of plasma detected by EFIRM correlated with those from saliva (FIG. 6B; R=0.94, P<0.0001 in the p.E746-A750del groups and R=0.92, P<0.0001 in the p.L858R groups).

TABLE 1

| | | Patient characteristics of testing group and blinded validation group. | | |
| --- | --- | --- | --- | --- |
| | | Non-blinded cohort | Blinded validation cohort | P value |
| Age | | 62.1 ± 12.7 | 58.8 ± 10.4 | 0.28[a] |
| Sex | Total | 22 | 40 | 1.00[b] |
| | Male | 12 (54.5%) | 22 (55.0%) | |
| | Female | 10 (45.5%) | 18 (45.0%) | |
| Smoker | | 7 (31.8%) | 11 (27.5%) | 0.95[b] |
| Stage | | | | 1.00[c] |
| | III | 5 (22.7%) | 8 (20.0%) | |
| | IV | 17 (77.3%) | 32 (80.0%) | |
| EGFR mutant type | | | | 0.98[b] |
| | Wild | 11 (50.0%) | 20 (50.0%) | |
| | L858R | 7 (31.8%) | 12 (30.0%) | |
| | Exon 19del | 4 (18.2%) | 8 (20.0%) | |

[a]T test;
[b]chi-square test;
[c]Fisher's test

TABLE 2

| | | | | Clinical characteristics and treatment course of four patients receiving TKI | | | | |
| --- | --- | --- | --- | --- | --- | --- | --- | --- |
| | Age | Sex | Stage | EGFR mutation | TKI use | Duration of TKI use (days) | Best clinical response | Current treatment |
| Case 1 | 68 | M | IV | Exon 19 Del | Afatinib | 391 | PR | Alimta + cisplatin |
| Case 2 | 49 | M | III | Exon 19 Del | Iressa | 335 | SD | Alimta + cisplatin |
| Case 3 | 77 | F | IV | Exon 19 Del | Iressa | 222 | PR | Iressa |
| Case 4 | 58 | F | IV | Exon 21 L858R | Iressa | 103 | SD | Alimta + cisplatin |

F, female;
M, male;
PR, partial response;
SD, stable disease p.L858R mutant group; P<0.0001). Similar results were obtained using a probe designed for the p.L858R mutant group (FIG. 4B; 113.2±75.1 in the p.L858R mutant group vs. 15.9±9.6 in the wild-type group and 9.5±3.2 in the p.E746-A750del group; P<0.0001). The receiver operating characteristic analysis (FIG. 5C) indicated that the AUCs were 0.94 (95% CI, 0.82-1) and 0.96 (95% CI, 0.90-1) (FIG. 5C) for probes carrying the p.E746-A750del or the p.L858R mutation, respectively.

Correlation of EGFR Mutation Status Between Plasma and Saliva Using EFIRM

The findings from the plasma were compared with those from the saliva to evaluate whether saliva could be as The amperometric currents of exon19 deletion group detected by EFIRM using an exon19 probe were significantly higher than those in the wild type and p.L858R mutant groups (FIG. 5A, 126.6.±58.57 in p.E746-A750del group versus 14.52±3.54 in wild type group and 9.61±3.67 in p.L858R mutant group, p<0.0001) Similar results are obtained using the probe designed for p.L858R mutant group (FIG. 5B, 113.2±75.06 in p.L858R mutant group versus 15.85±9.65 in wild type group and 9.54±3.24 in p.E746-A750del group, p<0.0001). Receiver operating characteristic analysis (FIG. 5C) indicated that for probes carrying the p.E746-A750del or the p.L858R mutation, the areas under the curve (AUCs) were 0.94 (95% CI, 0.82 to 1) and 0.96 (95% CI, 0.90 to 1) (FIG. 5C; Table 3), respectively. (Table 3).

TABLE 3

| Receiver operating characteristic analysis of TKI treatment. | | | |
| --- | --- | --- | --- |
| Explanation | AUC | Lower CI | Upper CI |
| AUC_Ex19Del_excluding_TKI | 0.9414 | 0.8245 | 1 |
| AUC_Ex19Del_w_TKI_as_wildtype | 0.9375 | 0.8133 | 1 |
| AUC_L858R_excluding_TKI | 0.9583 | 0.8994 | 1 |
| AUC_L858R_w_TKI_as_wildtype | 0.9505 | 0.882 | 1 |
| AUC_both_Probe_excluding_TKI | 0.9325 | 0.8538 | 1 |
| AUC_both_Probe_w_TKI_as_wildtype | 0.9229 | 0.8356 | 1 |

CI, confidence interval.

The System of the Present Invention for Oncogene Mutation Analysis

Current oncogene mutation detection technologies mainly PCR-based, requiring sample pretreatment and several hours of detection. Via the system of the present invention, EGFR mutations were accurately identified from circulating EGFR sequences. The system exploits (1) simple and effective biomarker release from body fluids, (2) enhanced sample mixing and accumulation, (3) enhanced hybridization of the EGFR gene, and (4) suppression of non-specific interference. When exposed to a non-uniform electrical field, DNA/RNA is rapidly released in situ. The specificity of each mutation is expected to yield a unique electric-field profile in terms of voltage, cycle numbers, duration, and other parameters. Positive potential in the electric field (cyclic square wave) facilitates accumulation of the gene target onto the working electrode, while negative potential removes weakly bound non-specific sequences. In addition to enhancing hybridization, the cyclic square wave electric field also generates near-field solution mixing and accumulation, due to the continuous flapping of the electrical field. The system only permits perfectly matched sequence hybridization; mismatched sequences are removed. By individually optimizing the electric profile for each target sequence of interest, the system achieves sensitivity and specificity that are comparable with those of quantitative PCR, while only requiring a few microliters of the clinical sample.

Currently it is not entirely clear how mechanistically tumor-specific oncogenic mutations are detected in saliva. In a previous study, it was demonstrated that breast cancer-derived microvesicles are capable of interacting with salivary gland cells, altering the composition of their secreted microvesicles (Lau C S, Wong D T. Breast Cancer Exosome-like Microvesicles and Salivary Gland Cells Interplay Alters Salivary Gland Cell-Derived Exosome-like Microvesicles In Vitro. *PLoS ONE* 2012; 7: e33037); inhibiting exosome biogenesis in pancreatic cancer results in the ablation of the development of discriminatory salivary biomarkers (Lau C, Kim Y, Chia D, et al. Role of Pancreatic Cancer-derived Exosomes in Salivary Biomarker Development *J Biol Chem* 2013; 288: 26888-26897). Recent investigations provide further evidence that exosomes carry not only protein, RNA, microRNA, mitochondrial DNA (Guescini M, Guidolin D, Vallorani L, et al. C2C12 myoblasts release micro-vesicles containing mtDNA and proteins involved in signal transduction. *Experimental cell research* 2010; 316: 1977-1984), and single-stranded DNA, but also large fragments of double-stranded mutated Kras and p53 DNA (Kahlert C, Melo S A, Protopopov A, et al. Identification of Double Stranded Genomic DNA Spanning all Chromosomes with Mutated KRAS and p53 DNA in the Serum Exosomes of Patients with Pancreatic Cancer. *The Journal of biological chemistry* 2014). More importantly, tumor-specific EGFRvIII was previously detected in serum microvesicles (Paez J G, Janne P A, Lee J C, et al. EGFR mutations in lung cancer: correlation with clinical response to gefitinib therapy. *Science* 2004; 304: 1497-1500) and was shown to be released into the blood to merge with the plasma membranes of cancer cells lacking EGFRvIII (Al-Nedawi K, Meehan B, Micallef J, et al. Intercellular transfer of the oncogenic receptor EGFRvIII by microvesicles derived from tumor cells. *Nature cell biology* 2008; 10: 619-624), it is reasonable to hypothesize that lung cancer cell-delivered microvesicles carrying EGFR DNA affect the DNA content of other cells, such as those in the salivary glands. However, the mechanisms by which lung-cancer cells release these microvesicles and disperse them via the blood to distant sites remain to be established.

The Influence of TKI Treatment on Detection of EGFR Mutations

During analysis of the correlation of detection of EGFR mutations in saliva from NSCLC patients, it was realized that four patients had previously undergone treatment with TKIs prior to enrolling in the study (Table 2). The amperometric currents of these four samples were significantly lower (10–25-nA) than the signal from NSCLC patients with the same EGFR mutations but no prior treatment with TKIs. The signals from the TKI-treated cases were similar to those patients with wildtype EGFR. It was hypothesized that TKI treatment effectively suppress the growth of NSCLC cells, leading to less tumor shedding of circulating tumor cells and/or shedding of mutated EGFR (free form or exosome bound), and effectively lesser detection by the system of the present invention in saliva. This is congruent with the present data. It should be noted that data analysis excluded these 4 TKI previously treated cases.

Current Clinical Practice for Detecting EGFR Mutations in NSCLC Patients

Direct sequencing of amplified DNA products is the most popular method for detecting EGFR mutations. This strategy often takes up to 3-4 weeks to yield results, and is clinically limited by low sensitivity and false negative or non-informative results, especially for cytology specimens. Several new techniques, including the use of TaqMan PCR, and denaturing high-performance liquid chromatography have been introduced (Janne P, Borras A, Kuang Y, et al. A rapid and sensitive enzymatic method for epidermal growth factor receptor mutation screening. *Clinical cancer research: an official journal of the American Association for Cancer Research* 2006; 12: 751-758; Chin T, Anuar D, Soo R, et al. Detection of epidermal growth factor receptor variations by partially denaturing HPLC. *Clin Chem* 2007; 53: 62-70;

Endo K, Konishi A, Sasaki H, et al. Epidermal growth factor receptor gene mutation in non-small cell lung cancer using highly sensitive and fast TaqMan PCR assay. *Lung Cancer* 2005; 50: 375-384), but none have been adopted as a standard clinical method for detecting EGFR mutations.

In addition, practical clinical obstacles often exist pertaining to the acquisition and availability of appropriate tissue samples as well as intratumoral genetic heterogeneity. In patients with advanced NSCLC, tumor tissue is not always available for EGFR mutation testing, either because only small amounts of tissue are collected or because the collected tissues have very low, or no, levels of tumor, according to CT-guided or bronchoscopic biopsy. Recent evidence suggests that regionally separated heterogeneous somatic mutational events can lead to sampling bias, which impairs the interpretation of genomics data derived from single-tumor biopsies (Gerlinger M, Rowan A J, Horswell S, et al. Intratumor heterogeneity and branched evolution revealed by multiregion sequencing. *The New England journal of medicine* 2012; 366: 883-892; Yap T A, Gerlinger M, Futreal P A, Pusztai L, Swanton C. Intratumor heterogeneity: seeing the wood for the trees. *Science translational medicine* 2012; 4: 127ps110). For patients who do not have enough tumor tissue for a mutation assay, or who are suspected of being associated with a false-negative result due to tumor heterogeneity within a tissue sample, body fluids-based EGFR mutation detection may substitute for tissue biopsy for molecular diagnosis.

Clinical Applications of the System of the Present Invention

Applying the system of the present invention to directly detect EGFR mutations from saliva of NSCLC patients will provide information on EGFR mutation status in a non-invasive, rapid and cost effective. These advantages will enable clinicians to adjust their therapeutic strategies in a timely fashion, consequently improving the clinical outcome of EGFR-targeting therapy. Since the system is based on an electrochemical platform, it can be easily transformed into high-throughput oncogenic mutation analysis lab assays as well as point-of-care devices for rapidly identifying oncogenic mutations on site. A portable point-of-care device that uses saliva samples for cancer detection based on this platform has already been developed (data and prototype not shown). In additional to assisting treatment decision making, the system also has the potential to diagnosis or screen for lung cancer. For patients who do not have enough tumor tissue for a mutation assay, mutation detection via the present invention may substitute for tissue biopsy. Another impactful application of the system technology is to address the well-known drug resistance eventually develops during the course of treatment with these EGFR-TKIs as a result of secondary mutations in the EGFR kinase domain, hampering the overall improvement in survival following EGFR-targeting treatment. The present invention is a non-invasive approach that will permit continuous monitoring of somatic EGFR mutations during lung-cancer progression. Thirdly, for patients with lung nodule, the platform will be helpful in differential diagnosis. Finally, the system has the potential to screen for lung cancer, particularly in people who have never smoked. Although most lung cancers result from smoking, ~25% of lung-cancer cases worldwide occur in people who have never smoked, accounting for >300,000 deaths each year (Sun S, Schiller J H, Gazdar A F. Lung cancer in never smokers—a different disease. *Nature reviews Cancer* 2007; 7: 778-790; Wakelee H A, Chang E T, Gomez S L, et al. Lung cancer incidence in never smokers. *Journal of clinical oncology: official journal of the American Society of Clinical Oncology* 2007; 25: 472-478). Following consideration of the amount of exposure to cigarette smoke, low-dose CT-based examination has been proposed for high-risk subjects to provide an early diagnosis of lung cancer (Boiselle P M. Computed tomography screening for lung cancer. *JAMA: the journal of the American Medical Association* 2013; 309: 1163-1170). For people who have never smoked, however, no ideal method has been established to detect those at high risk of cancer. EGFR mutations are the first specific genetic mutations to be associated with cancer in patients who have never smoked, and increasing smoke exposure is negatively correlated with EGFR mutation status (Pham D, Kris M G, Riely G J, et al. Use of cigarette-smoking history to estimate the likelihood of mutations in epidermal growth factor receptor gene exons 19 and 21 in lung adenocarcinomas. *Journal of clinical oncology: official journal of the American Society of Clinical Oncology* 2006; 24: 1700-1704). Compared to blood sampling for detecting circulating DNA, collecting saliva is non-invasive, and therefore using the present invention to detect EGFR mutations will be advantageous to blood-based diagnosis in the screening of early lung cancers, especially in people who have never smoked.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of detecting lung cancer in a subject comprising:

obtaining a sample from the subject;

mixing a first portion of the sample with a solution comprising a labeled detector probe;

adding the mixture to a first electrode chip on a device, the electrode chip comprising a working electrode, a counter electrode, and a reference electrode; wherein the working electrode is coated with a conducting polymer embedded with a capture probe capable of binding to a marker associated with lung cancer in the sample;

generating 5 cycles to about 10 cycles of a cyclic square wave electric fields field across the electrode for each surface reaction; and measuring the current in the electrode chip, wherein a change in current is correlated to the presence of the marker associated with lung cancer in the sample wherein the capture and detection probes are selected from the group consisting of i) the capture probe comprises the nucleotide sequence of SEQ ID NO: 1 and the detector probe comprises the nucleotide sequence of SEQ ID NO: 2; and ii) the capture probe comprises the nucleotide sequence of SEQ ID NO: 3 and the detector probe comprises the nucleotide sequence of SEQ ID NO: 4.

2. The method of claim 1, wherein the sample is selected from the group consisting of a saliva sample and a blood sample.

3. The method of claim 1, wherein the change in current in the sample is measurable within 10 minutes after the sample has been loaded into the well.

* * * * *

SEQUENCE LISTING

```
Sequence total quantity: 4
SEQ ID NO: 1          moltype = DNA  length = 22
FEATURE               Location/Qualifiers
misc_feature          1..22
                      note = Chemically Synthesized
source                1..22
                      mol_type = other DNA
                      organism = synthetic construct
SEQUENCE: 1
tgttgcttcc ttgatagcga cg                                        22

SEQ ID NO: 2          moltype = DNA  length = 21
FEATURE               Location/Qualifiers
misc_feature          1..21
                      note = Chemically Synthesized
```

-continued

```
source                    1..21
                          mol_type = other DNA
                          organism = synthetic construct
SEQUENCE: 2
ggaattttaa ctttctcacc t                                        21

SEQ ID NO: 3              moltype = DNA  length = 21
FEATURE                   Location/Qualifiers
misc_feature              1..21
                          note = Chemically Synthesized
source                    1..21
                          mol_type = other DNA
                          organism = synthetic construct
SEQUENCE: 3
cagtttggcc cgcccaaaat c                                        21

SEQ ID NO: 4              moltype = DNA  length = 22
FEATURE                   Location/Qualifiers
misc_feature              1..22
                          note = Chemically Synthesized
source                    1..22
                          mol_type = other DNA
                          organism = synthetic construct
SEQUENCE: 4
ttgacatgct gcggtgtttt ca                                       22
```